United States Patent
Daunert et al.

(10) Patent No.: US 7,345,160 B2
(45) Date of Patent: Mar. 18, 2008

(54) AEQUORIN AND OBELIN MUTANTS WITH DIFFERING WAVELENGTHS AND BIOLUMINESCENCE

(75) Inventors: Sylvia Daunert, Lexington, KY (US); Sapna Kamlakar Deo, Lexington, KY (US); Emre Dikici, Lexington, KY (US); Laura Rowe, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 391 days.

(21) Appl. No.: 10/811,138

(22) Filed: Mar. 29, 2004

(65) Prior Publication Data

US 2005/0214776 A1     Sep. 29, 2005

(51) Int. Cl.
*C07H 21/04* (2006.01)
*C12P 21/02* (2006.01)
*C07K 14/435* (2006.01)

(52) U.S. Cl. .............. 536/23.5; 435/69.1; 530/350
(58) Field of Classification Search ............... 536/23.5; 435/69.1; 530/350
See application file for complete search history.

(56) References Cited

U.S. PATENT DOCUMENTS

| | | |
|---|---|---|
| 5,023,181 A | 6/1991 | Inouye |
| 5,093,240 A | 3/1992 | Inouye et al. |
| 5,139,937 A | 8/1992 | Inouye et al. |
| 5,162,227 A | 11/1992 | Cormier |
| 5,360,728 A | 11/1994 | Prasher |
| 5,422,266 A | 6/1995 | Cormier et al. |
| 5,491,084 A | 2/1996 | Chalfie et al. |
| 5,541,309 A | 7/1996 | Prasher |
| 5,744,579 A | 4/1998 | Cormier et al. |
| 5,766,941 A | 6/1998 | Cormier et al. |
| 5,798,441 A | 8/1998 | Cormier et al. |
| 5,876,995 A * | 3/1999 | Bryan ..................... 435/189 |

FOREIGN PATENT DOCUMENTS

| | | |
|---|---|---|
| EP | 0 226 979 A2 | 7/1987 |
| EP | 0 245 093 A1 | 11/1987 |
| EP | 0 245 093 B1 | 11/1987 |
| EP | 0 540 064 A1 | 5/1993 |

OTHER PUBLICATIONS

Current Protocols in Molecular Biology, Ausubel et al., eds., Unit 6.3, John Wiley & Sons, Inc., Hoboken, New Jersey, 1993, printed from the Internet on Apr. 23, 2007.*

(Continued)

*Primary Examiner*—Rebecca E. Prouty
*Assistant Examiner*—Rosanne Kosson
(74) *Attorney, Agent, or Firm*—McDermott Will & Emery LLP

(57) ABSTRACT

The invention relates to aequorin and obelin mutants whose emission is shifted with respect to wild type. The shift in emission is accomplished using a combination of mutations of amino acids within aequorin or obelin that affect bioluminescence; use of different types of chromophores, i.e., coelenterazines with variable emission characteristics; and modifications of the photoprotein with fluorophores that will allow for emission of light at longer wavelengths as a result of energy transfer. Additionally, an assay employing aequorin mutants to test for HIV-1 protease inhibitors is disclosed.

2 Claims, 18 Drawing Sheets a table showing the emission wavelength maximum (nm) of aequorin mutants with coelenterazine analogues.

| Coelenterazine Analogue | Wild Type Aequorin | Aequorin Mutant S (Aeq3) | Aequorin Mutant S Ser5Cys (Aeq5) | Aequorin Mutant S Tyr132Ile |
|---|---|---|---|---|
| CTZ i | 472 | 491 | 491 | 487 |
| CTZ ip | 472 | 470 | 454 | 453 |
| CTZ h | 472 | 476 | 471 | 471 |
| CTZ hcp | 472 | 476 | 448 | 465 |
| CTZ cp | 472 | 470 | 456 | 457 |
| CTZ fcp | 472 | 466 | 471 | 471 |
| CTZ f | 472 | 490 | 473 | 471 |
| CTZ n | 472 | 487 | | |
| CTZ native | 472 | 474 | 471 | 471 |

* All values, except wild type aequorin, were calculated from the average of 3 trials (wild type with 2). All mutants were, except Aeq5 purified to >95% purity. CTZ analogues diluted to 100 micrograms/ml methanol.

OTHER PUBLICATIONS

Shimomura, O., et al. "Light-emitting properties of recombinant semi-synthetic aequorins and recombinant fluorescein-conjugated aequorin for measuring cellular calcium" Cell Calcium (1993) 14, pp. 373-378.

Kurose, K., et al. "Bioluminesence of the $Ca^{2+}$-binding photoprotein aequorin after cysteine modification" Proc. Natl. Acad. Sci. USA, Jan. 1989, vol. 86, pp. 80-84.

Lewis, J.C., et al. "Bioluminescence and Secondary Structure Properties of Aequorin Mutants Produced for Site-Specific Conjugation and Immobilization" Bioconjugate Chem, 2000, American Chemical Society, 11, pp. 65-70.

Shrestha, S., et al. "Cysteine-Free Mutant of Aequorin as a Photolabel in Immunoassay Development" Bioconjugate Chem. 2002, American Chemical Society, 13, pp. 269-275.

Tsuji, Frederick I., et al. "Site-specific mutagenesis of the calcium-binding photoprotein aequorin" Proc. Natl. Acad. Sci. USA, vol. 83, pp. 8107-8111, Nov. 1986.

Prasher, Douglas, et al. "Cloning and Expression of the cDNA Coding for Aequorin, A Bioluminescent Calcium-Binding Protein," Biochemical and Biophysical Research Communications, vol. 126, No. 3, 1985, pp. 1259-1268.

Prasher, Douglas C., et al. "Isolation and Expression of a cDNA Coding for Aequorin, the $Ca^{2+}$-Activated Photoprotein from *Aequorea victoria*" Methods in Enzymology, 1986, vol. 133, pp. 288-297.

Prasher, Douglas C., et al., "Sequence Comparisons of Complementary DNAs Encoding Aequorin Isotypes" Biochemistry 1987, 26, pp. 1326-1332.

Charbonneau, Harry, et al. "Amino Acid Sequence of the Calcium-Dependent Photoprotein Aequorin"Biochemistry 1985, 24, pp. 6762-6771.

Shimomura, Osamu et al. "Resistivity to denaturation of the apoprotein of aequorin and reconstitution of the luminescent photoprotein from the partially denaturated apoprotein" Biochem. J. (1981) 199, pp. 825-828.

Inouye, Satoshi, et al. "Overexpression and Purification of the Recombinant $Ca^{2+}$-Binding Protein, Apoaequorin" J. Biochem. 105 (1989) pp. 473-477.

Inouye, Satoshi, et al. "Expression of Apoaequorin Complementary DNA in *Escherichia coli*" Biochemistry 1986, 25, pp. 8425-8429.

Inouye, Satoshi, et al. "Cloning and sequence analysis of cDNA for the luminescent protein aequorin" Proc. Natl. Acad. Sci. USA, vol. 82, pp. 3154-3158, May 1985.

Prendergast, Franklyn G., et al. "Chemical and Physical Properties of Aequorin and the Green Fluorescent Protein Isolated from *Aequorea forskåloe*" J. Am. Chem. Soc. vol. 17, No. 17, 1978, pp. 3448-3453.

Deo, Sapna K., et al. "Bioluminescence Detection of Proteolytic Bond Cleavage by Using Recombinant Aequorin" Analytical Biochemistry 281, pp. 87-94 (2000).

Malikova, Natalia, P., et al. "Spectral tuning of obelin bioluminescence by mutations of Trp92" FEBS Letters 554 (2003) pp. 184-188.

Vysotski et al. "Violet bioluminescence and fast kinetics from W92F obelin: structure-based proposals for the bioluminescence triggering and the identification of the emitting species," Biochemistry, 2003 May 27, 2003, 42(20) pp. 6013-6024.

Bondar, et al. "Role of conservative residue Cys158 in the formation of an active photoprotein complex of obelin" Biochemistry (Moscow) vol. 66, No. 9, pp. 1014-1018.

Ohmiya et al. "Two excited states in aequorin bioluminescence induced by tryptophan modification" FEBS, vol. 301, No. 2, Apr. 1992, pp. 197-201.

Ohmiya et al. "Bioluminescence of the $Ca^{2+}$-binding photoprotein, aequorin, after histidine modification" FEBS, vol. 320, No. 3, Apr. 1993, pp. 267-270.

Lewis, J.C., et al. "Bioluminescence and Secondary Structure Properties of Aequorin Mutants Produced for Site-Specific Conjugation and Immobilization" Bioconjugate Chem. 2000, 11, pp. 65-70.

\* cited by examiner

Fig. 1

Fig. 1 is a table showing the emission wavelength maximum (nm) of aequorin mutants with coelenterazine analogues.

| Coelenterazine Analogue | Wild Type Aequorin | Aequorin Mutant S (Aeq3) | Aequorin Mutant S Ser5Cys (Aeq5) | Aequorin Mutant S Tyr132Ile |
|---|---|---|---|---|
| CTZ i | 472 | 491 | 491 | 487 |
| CTZ ip | 472 | 470 | 454 | 453 |
| CTZ h | 472 | 476 | 471 | 471 |
| CTZ hcp | 472 | 476 | 448 | 465 |
| CTZ cp | 472 | 470 | 456 | 457 |
| CTZ fcp | 472 | 466 | 471 | 471 |
| CTZ f | 472 | 490 | 473 | 471 |
| CTZ n | 472 | 487 | | |
| CTZ native | 472 | 474 | 471 | 471 |

\* All values, except wild type aequorin, were calculated from the average of 3 trials (wild type with 2). All mutants were, except Aeq5 purified to >95% purity. CTZ analogues diluted to 100 micrograms/ml methanol.

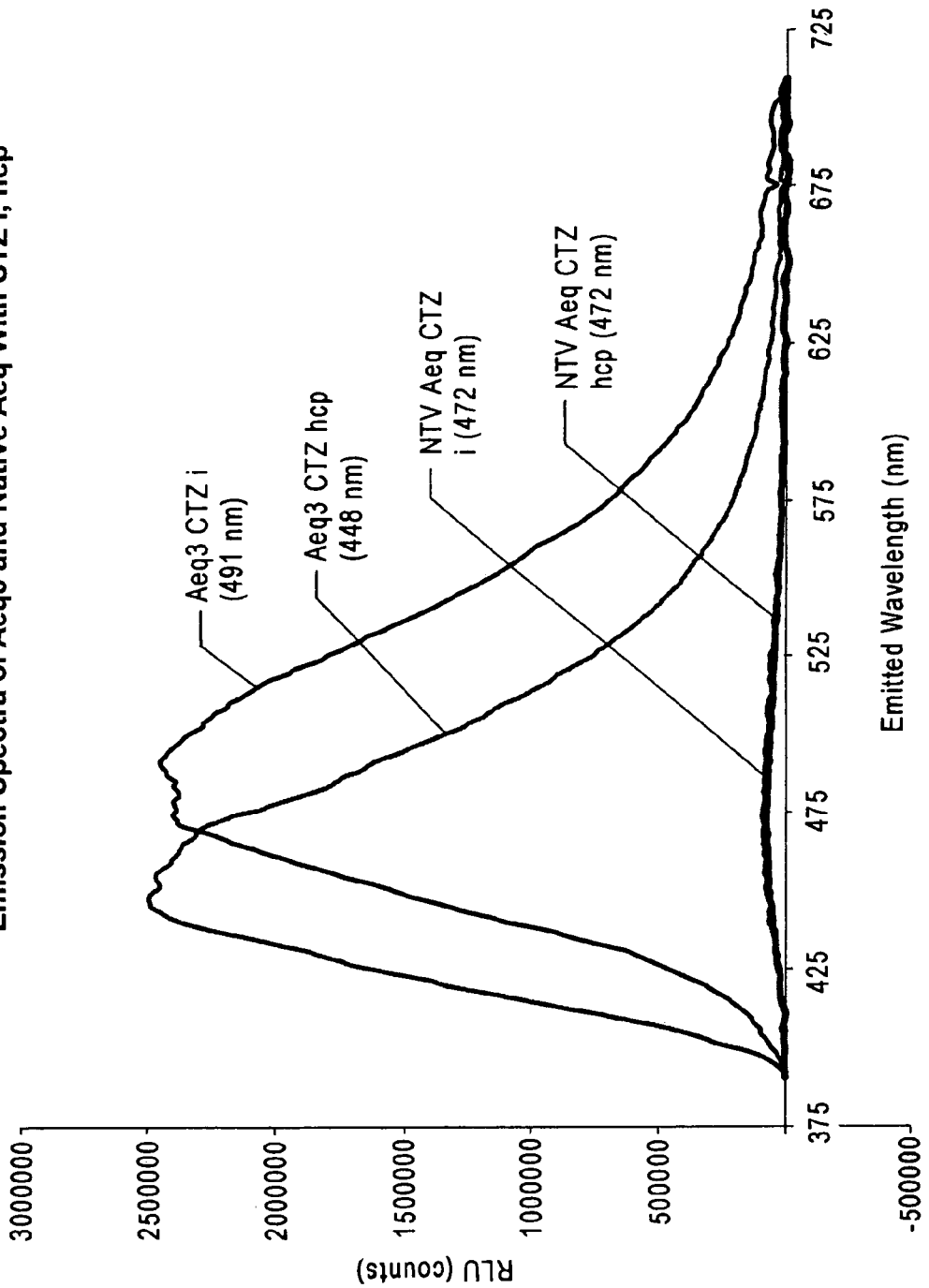

Aequorin 3 With Coelenterazine (CTZ) Analogues

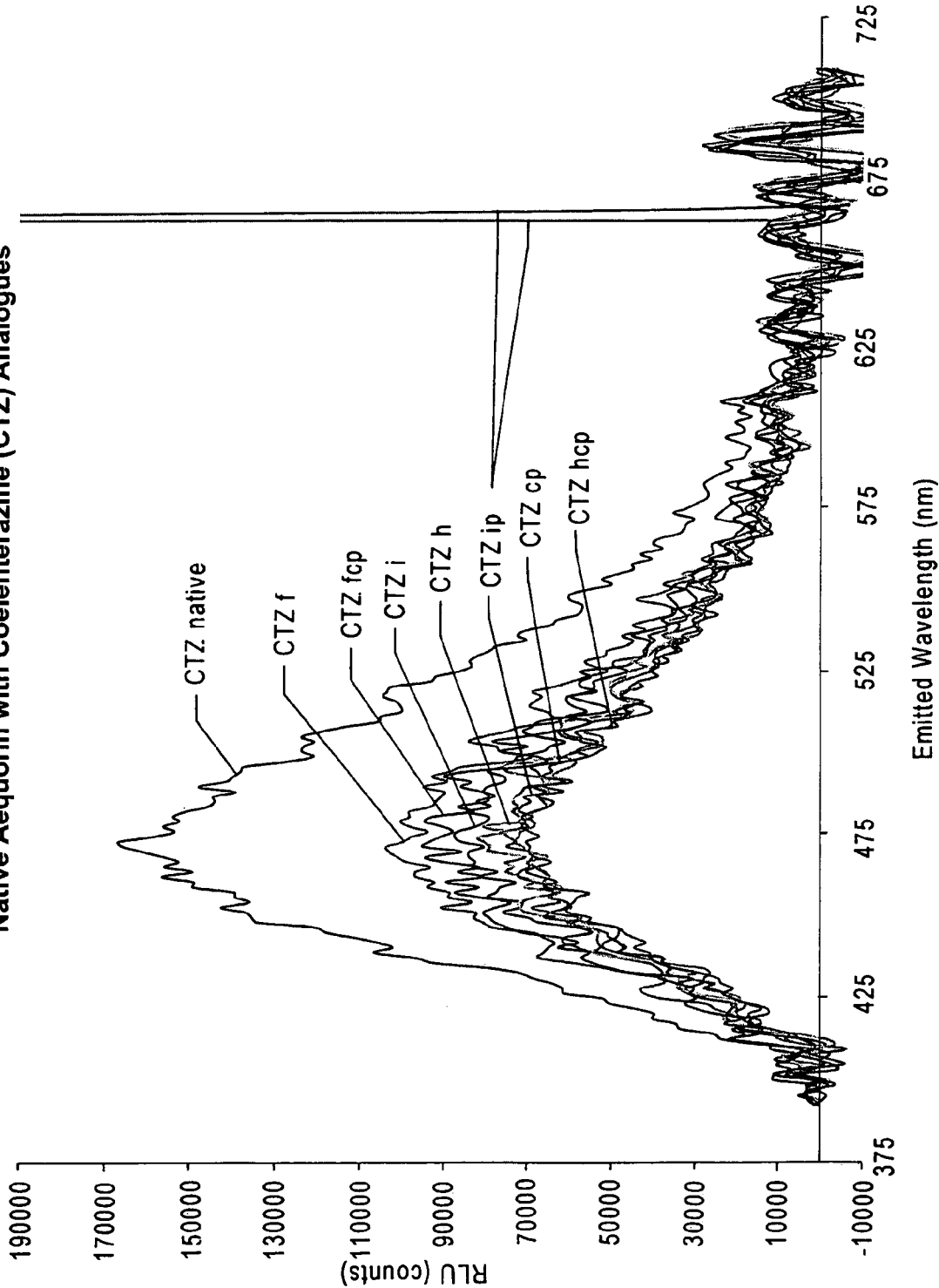

Fig. 7

Fig. 7 is a table showing the emission wavelength maximum (nm) of aequorin mutant Mutant S Y132I, Mutant S having a 3-fluoro-1-tyrosine aequorin or a 5-fluoro-1-tyrosine non-natural amino acid in position 132 in conjunction with coelenterazine analogues CTZ i, ip, n, h, hcp, cp, fcp, f and native CTZ.

| Coelenterazine Analogue | Wild Type Aequorin | Aequorin Mutant S Tyr132Ile | Aequorin Mutant S Tyr132 3-fluoro-l-tyr | Aequorin Mutant S Tyr132 5-fluoro-l-trp |
|---|---|---|---|---|
| CTZ i | 472 | 491 | 511 | 495 |
| CTZ ip | 472 | 452 | 471 | |
| CTZ n | 472 | 491 | 500 | |
| CTZ h | 472 | 472 | 498 | 471 |
| CTZ hcp | 472 | 452 | 471 | 468 |
| CTZ cp | 472 | 457 | 471 | 471 |
| CTZ fcp | 472 | 463 | 471 | |
| CTZ f | 472 | 472 | 500 | 497 |
| CTZ native | 472 | 471 | 495 | 472 |

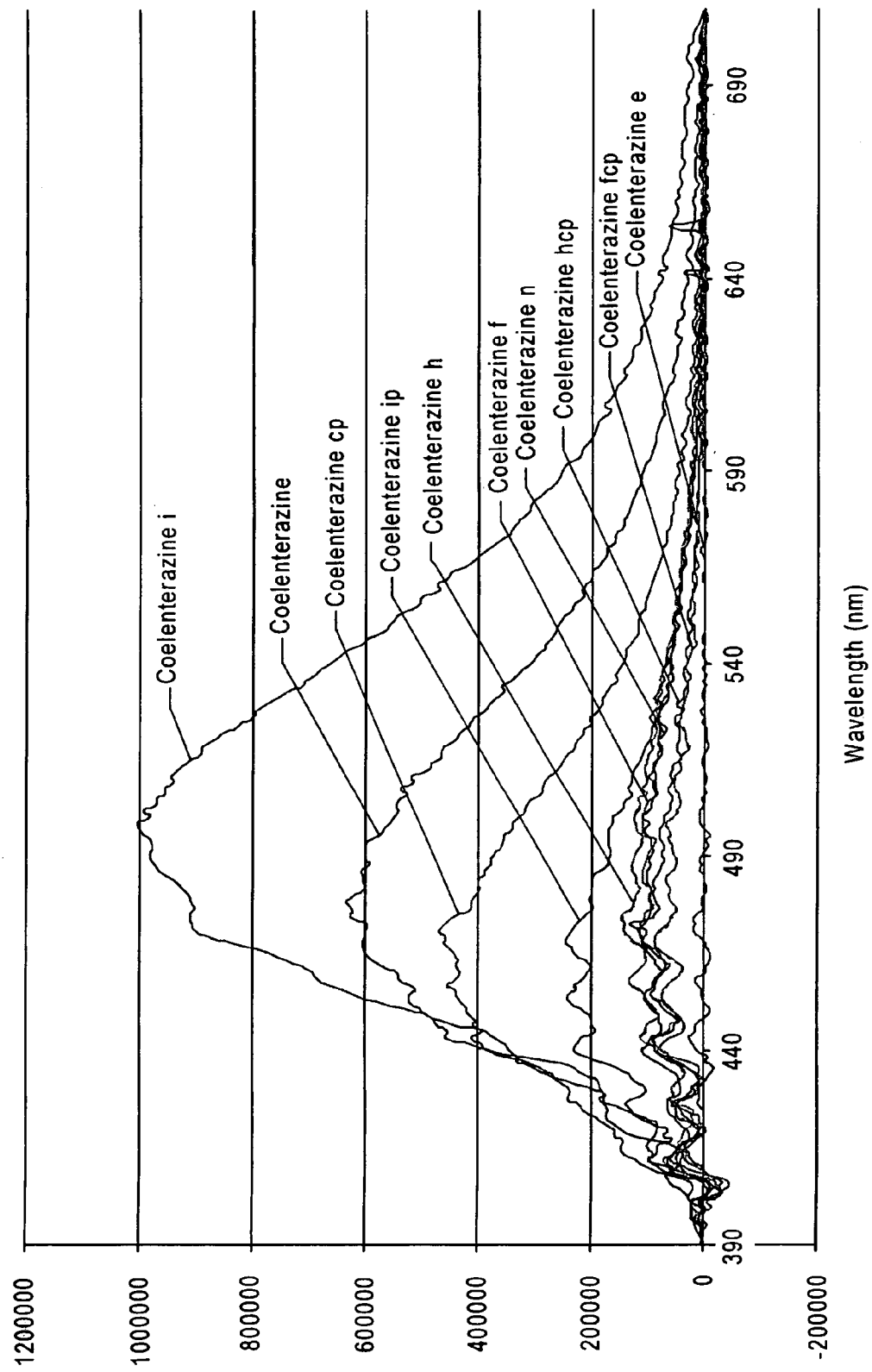

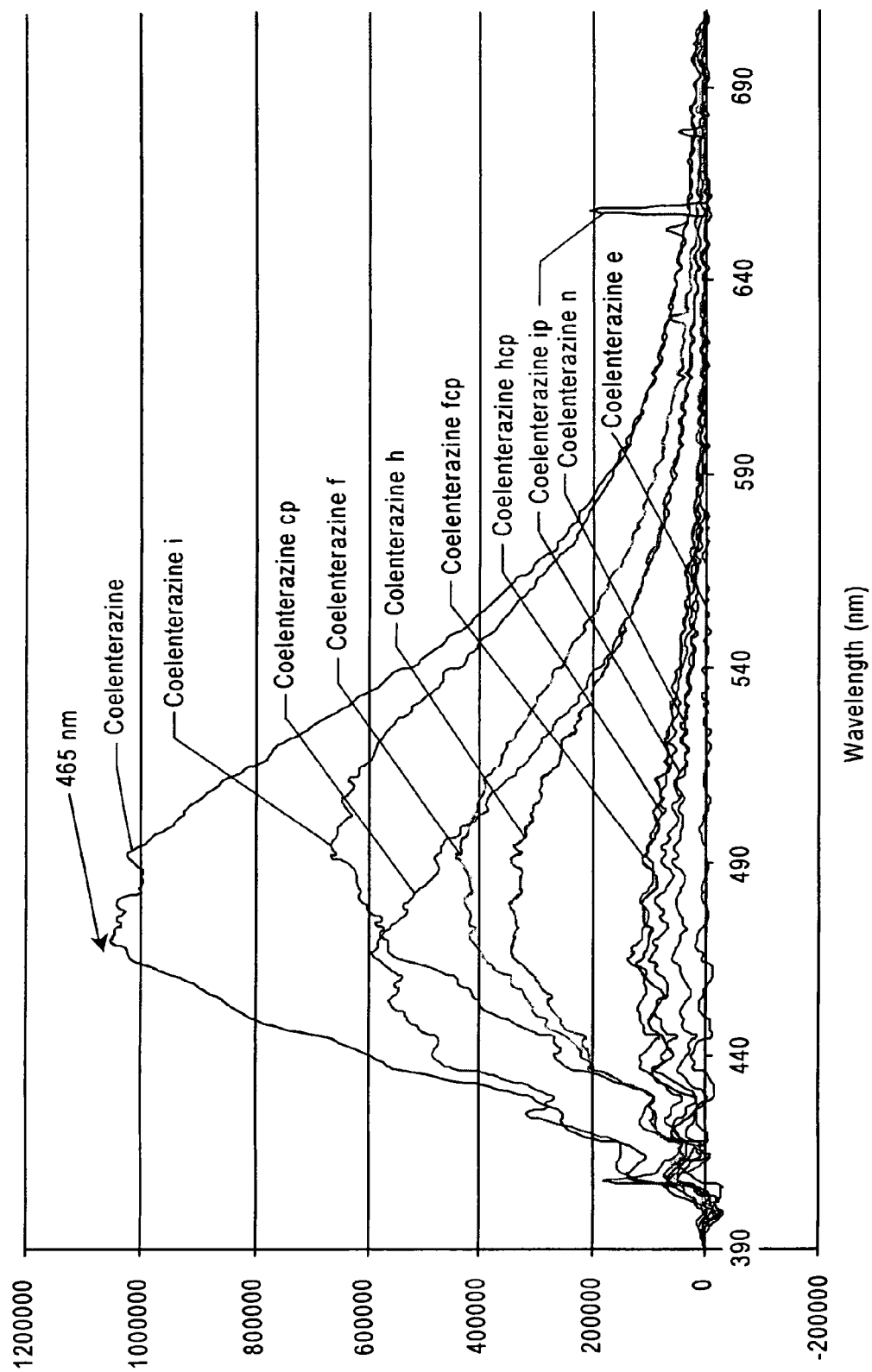

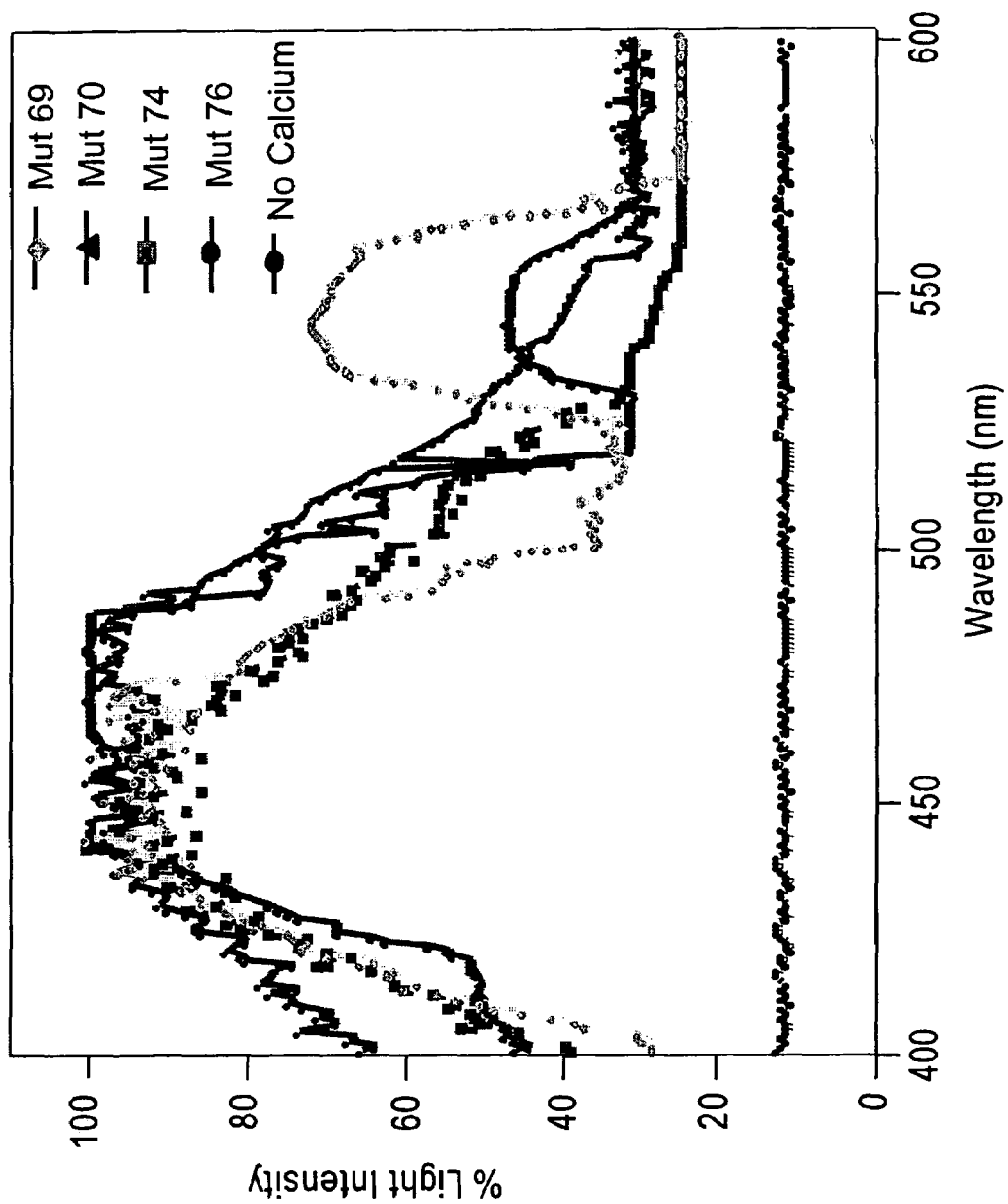

Fig. 11

SEQ ID NO: 1 cDNA encoding wild type apoaequorin

```
  1 aatgcaattc atctttgcat caaagaatta catcaaatct ctagttgatc aactaaattg
 61 tctcgacaac aacaagcaaa catgacaagc aaacaatact cagtcaagct tacatcagac
121 ttcgacaacc caagatggat tggacgacac aagcatatgt tcaatttcct tgatgtcaac
181 cacaatggaa aaatctctct tgacgagatg gtctacaagg catctgatat tgtcatcaat
241 aaccttggag caacacctga gcaagccaaa cgacacaaag atgctgtaga agccttcttc
301 ggaggagctg gaatgaaata tggtgtggaa actgattggc ctgcatatat tgaaggatgg
361 aaaaaattgg ctactgatga attggagaaa tacgccaaaa acgaaccaac gctcatccgt
421 atatggggtg atgctttgtt tgatatcgtt gacaaagatc aaaatggagc cattacactg
481 gatgaatgga agcatacac caaagctgct ggtatcatcc aatcatcaga agattgcgag
541 gaaacattca gagtgtgcga tattgatgaa agtggacaac tcgatgttga tgagatgaca
601 agacaacatt taggattttg gtacaccatg gatcctgctt gcgaaaagct ctacggtgga
661 gctgtcccct aagaagctct acggtggtga tgcaccctgg gaagatgatg tgattttgaa
721 taaaacactg atgaattcaa tcaaaatttt ccaaattttt gaacgatttc aatcgtttgt
781 gttgattttt gtaattagga acagattaaa tcgaatgatt agttgttttt ttaatcaaca
841 gaacttacaa atcgaaaaag t
```

Fig. 12

SEQ ID NO: 2 amino acid sequence for wild type apoaequorin

```
VKLTSDFDNP RWIGRHKHMF NFLDVNHNGK ISLDEMVYKA SDIVINNLGA
TPEQAKRHKD AVEAFFGGAG MKYGVETDWP AYIEGWKKLA TDELEKYAKN
EPTLIRIWGD ALFDIVDKDQ NGAITLDEWK AYTKAAGIIQ SSEDCEETFR
VCDIDESGQL DVDEMTRQHL GFWYTMDPAC EKLYGGAVP
```

Fig. 13

SEQ ID NO: 3 cDNA encoding Mutant S apoaequorin

```
  1 aatgcaattc atctttgcat caaagaatta catcaaatct
ctagttgatc aactaaattg
 61 tctcgacaac aacaagcaaa catgacaagc aaacaatact
cagtcaagct tacatcagac
121 ttcgacaacc caagatggat tggacgacac aagcatatgt
tcaatttcct tgatgtcaac
181 cacaatggaa aatctctct tgacgagatg gtctacaagg
catctgatat tgtcatcaat
241 aaccttggag caacacctga gcaagccaaa cgacacaaag
atgctgtaga agccttcttc
301 ggaggagctg aatgaaata tggtgtggaa actgattggc
ctgcatatat tgaaggatgg
361 aaaaaattgg ctactgatga attggagaaa tacgccaaaa
acgaaccaac gctcatccgt
421 atatggggtg atgctttgtt tgatatcgtt gacaaagatc
aaaatggagc cattacactg
481 gatgaatgga agcatacac caaagctgct ggtatcatcc
aatcatcaga agatagcgag
541 gaaacattca gagtgagcga tattgatgaa agtggacaac
tcgatgttga tgagatgaca
601 agacaacatt taggattttg gtacaccatg gatcctgcta
gcgaaaagct ctacggtgga
661 gctgtcccct aagaagctct acggtggtga tgcaccctgg
gaagatgatg tgattttgaa
721 taaaacactg atgaattcaa tcaaaatttt ccaaattttt
gaacgatttc aatcgtttgt
781 gttgattttt gtaattagga acagattaaa tcgaatgatt
agttgttttt ttaatcaaca
841 gaacttacaa atcgaaaaag t
```

Fig. 14

SEQ ID NO: 4 amino acid sequence for "Mutant S" apoaequorin

VKLTSDFDNP RWIGRHKHMF NFLDVNHNGK ISLDEMVYKA SDIVINNLGA
TPEQAKRHKD AVEAFFGGAG MKYGVETDWP AYIEGWKKLA TDELEKYAKN
EPTLIRIWGD ALFDIVDKDQ NGAITLDEWK AYTKAAGIIQ SSEDSEETFR
VSDIDESGQL DVDEMTRQHL GFWYTMDPAS EKLYGGAVP

Plasmid construct for the expression of the aequorin fusion protein and schematic representation of the fusion protein showing the HIV-1 protease cleavage site. B represents biotin and NA represents Neutravidin immobilized on the wells.

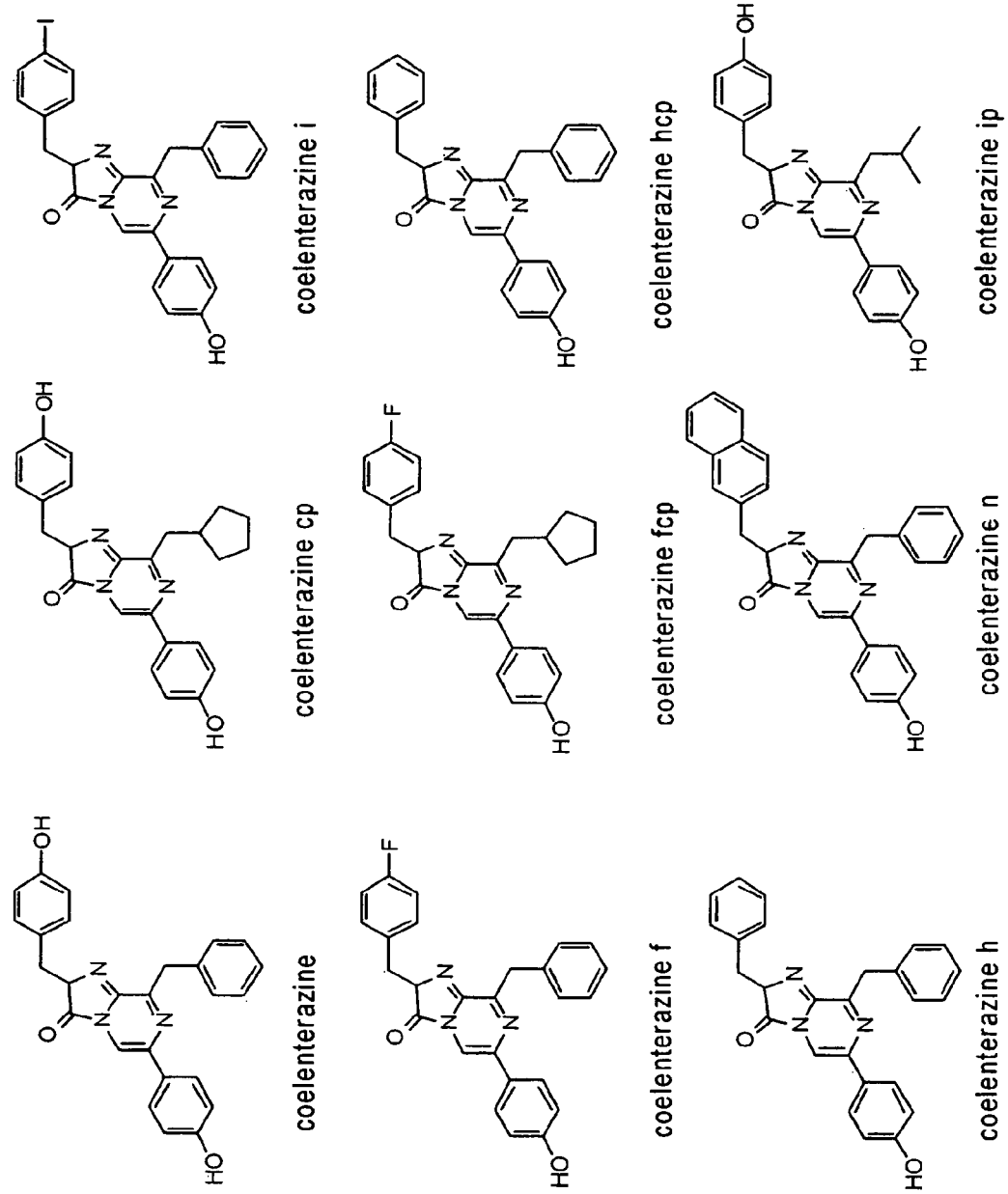
Fig. 16 Coelenterazine Analogs

Fig. 17. Non-natural amino acids

| Non-natural Amino Acid Analogue | Representative Example | Effect |
|---|---|---|
| Fluoro-analogue |  3-fluoro-L-tyrosine | Altered $pK_a$ and H-bonding strength |
| Amine-analogue | 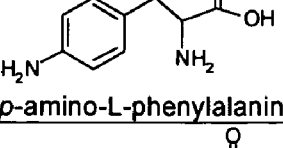 p-amino-L-phenylalanine | Altered electrostatic charge and H-bonding strength |
| Alkyl-analogue |  p-methoxy-L-phenylalanine | Altered H-bonding capability, increased bulkiness |
| Nitro-analogue | 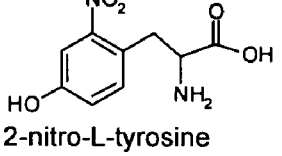 2-nitro-L-tyrosine | Altered π-character, altered $pK_a$, altered H-bonding strength, and steric effects |
| Hydroxyl-analogue | 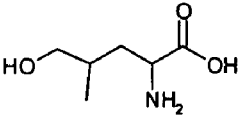 2-amino-5-hydroxy-4-methyl pentanoic acid | Altered $pK_a$, loss of π–π interactions |

Fig. 18 SEQ ID NO: 5, Obelin cDNA sequence

```
  1 acgatcgaac caaacaactc agctcacagc tactgaacaa ctcttgttgt gtacaatcaa
 61 aatgtcttca aaatacgcag ttaaactcaa gactgacttt gataatccac gatggatcaa
121 aagacacaag cacatgtttg atttcctcga catcaatgga aatggaaaaa tcaccctcga
181 tgaaattgtg tccaaggcat ctgatgacat atgtgccaag ctcgaagcca caccagaaca
241 aacaaaacgc catcaagttt gtgttgaagc tttctttaga ggatgtggaa tggaatatgg
301 taaagaaatt gccttcccac aattcctcga tggatggaaa caattggcga cttcagaact
361 caagaaatgg gcaagaaacg aacctactct cattcgtgaa tggggagatg ctgtctttga
421 tatttcgac aaagatggaa gtggtacaat cactttggac gaatggaaag cttatggaaa
481 aatctctggt atctctccat cacaagaaga ttgtgaagcg acatttcgac attgcgattt
541 ggacaacagt ggtgaccttg atgttgacga gatgacaaga caacatcttg gattctggta
601 cactttggac ccagaagctg atggtctcta tggcaacgga gttccctaag ctttttttcg
661 aa
```

Fig. 19. SEQ ID NO: 6, Native Obelin Amino Acid Sequence

```
MSSKYAVKLK  TDFDNPRWIK  RHKHMFDFLD  INGNGKITLD  EIVSKASDDI
CAKLEATPEQ  TKRHQVCVEA  FFRGCGMEYG  KEIAFPQFLD  GWKQLATSEL
KKWARNEPTL  IREWGDAVFD  IFDKDGSGTI  TLDEWKAYGK  ISGISPSQED
CEATFRHCDL  DNSGDLDVDE  MTRQHLGFWY  TLDPEADGLY  GNGVP
```

Fig. 20 Obelin mutants with Coelenerazine analogues.

|  | Coelenterazine Analogs Emission Max (nm) | | | | | | | |
|---|---|---|---|---|---|---|---|---|
| Obelin Mutant | *i* | *ip* | *h* | *hcp* | *cp* | *fcp* | *f* | *ctz* |
| C75S-C51S | 521 | 478 | 503 | 478 | 472 | 497 | 503 | 491 |
| C75S-C67S | 505 | 471 | 500 | 471 | 471 | 487 | 504 | 491 |
| C158S | 506 | 472 | 497 | 478 | 472 | 475 | 497 | 491 |
| C151S | 497 | 471 | 490 | 471 | 471 | 474 | 493 | 491 |

SEQUENCE LISTING

<160> NUMBER OF SEQ ID NOS: 6

<210> SEQ ID NO 1
<211> LENGTH: 861
<212> TYPE: DNA
<213> ORGANISM: Aequorea victoria

<400> SEQUENCE: 1

```
aatgcaattc atctttgcat caaagaatta catcaaatct ctagttgatc aactaaattg      60
tctcgacaac aacaagcaaa catgacaagc aaacaatact cagtcaagct tacatcagac     120
ttcgacaacc caagatggat tggacgacac aagcatatgt tcaatttcct tgatgtcaac     180
cacaatggaa aaatctctct tgacgagatg gtctacaagg catctgatat tgtcatcaat     240
```

```
aaccttggag caacacctga gcaagccaaa cgacacaaag atgctgtaga agccttcttc    300
ggaggagctg gaatgaaata tggtgtggaa actgattggc ctgcatatat tgaaggatgg    360
aaaaaattgg ctactgatga attggagaaa tacgccaaaa acgaaccaac gctcatccgt    420
atatggggtg atgctttgtt tgatatcgtt gacaaagatc aaaatggagc cattacactg    480
gatgaatgga agcatacac caaagctgct ggtatcatcc aatcatcaga agattgcgag    540
gaaacattca gagtgtgcga tattgatgaa agtggacaac tcgatgttga tgagatgaca    600
agacaacatt taggattttg gtacaccatg gatcctgctt gcgaaaagct ctacggtgga    660
gctgtcccct aagaagctct acggtggtga tgcaccctgg aagatgatg tgattttgaa     720 taaaacactg atgaattcaa tcaaaatttt ccaaattttt gaacgatttc aatcgtttgt    780
gttgattttt gtaattagga acagattaaa tcgaatgatt agttgttttt ttaatcaaca    840
gaacttacaa atcgaaaaag t                                              861
```

<210> SEQ ID NO 2
<211> LENGTH: 189
<212> TYPE: PRT
<213> ORGANISM: Aequorea victoria

<400> SEQUENCE: 2

```
Val Lys Leu Thr Ser Asp Phe Asp Asn Pro Arg Trp Ile Gly Arg His
1               5                   10                  15

Lys His Met Phe Asn Phe Leu Asp Val Asn His Asn Gly Lys Ile Ser
            20                  25                  30

Leu Asp Glu Met Val Tyr Lys Ala Ser Asp Ile Val Ile Asn Asn Leu
        35                  40                  45

Gly Ala Thr Pro Glu Gln Ala Lys Arg His Lys Asp Ala Val Glu Ala
    50                  55                  60

Phe Phe Gly Gly Ala Gly Met Lys Tyr Gly Val Glu Thr Asp Trp Pro
65                  70                  75                  80

Ala Tyr Ile Glu Gly Trp Lys Lys Leu Ala Thr Asp Glu Leu Glu Lys
                85                  90                  95

Tyr Ala Lys Asn Glu Pro Thr Leu Ile Arg Ile Trp Gly Asp Ala Leu
            100                 105                 110

Phe Asp Ile Val Asp Lys Asp Gln Asn Gly Ala Ile Thr Leu Asp Glu
        115                 120                 125

Trp Lys Ala Tyr Thr Lys Ala Ala Gly Ile Ile Gln Ser Ser Glu Asp
    130                 135                 140

Cys Glu Glu Thr Phe Arg Val Cys Asp Ile Asp Glu Ser Gly Gln Leu
145                 150                 155                 160

Asp Val Asp Glu Met Thr Arg Gln His Leu Gly Phe Trp Tyr Thr Met
                165                 170                 175

Asp Pro Ala Cys Glu Lys Leu Tyr Gly Gly Ala Val Pro
            180                 185
```

<210> SEQ ID NO 3
<211> LENGTH: 861
<212> TYPE: DNA
<213> ORGANISM: Aequorea victoria

<400> SEQUENCE: 3

```
aatgcaattc atctttgcat caaagaatta catcaaatct ctagttgatc aactaaattg     60
tctcgacaac aacaagcaaa catgacaagc aaacaatact cagtcaagct tacatcagac    120
ttcgacaacc caagatggat tggacgacac aagcatatgt tcaatttcct tgatgtcaac    180
```

```
cacaatggaa aaatctctct tgacgagatg gtctacaagg catctgatat tgtcatcaat    240
aaccttggag caacacctga gcaagccaaa cgacacaaag atgctgtaga agccttcttc    300
ggaggagctg gaatgaaata tggtgtggaa actgattggc ctgcatatat tgaaggatgg    360
aaaaaattgg ctactgatga attggagaaa tacgccaaaa acgaaccaac gctcatccgt    420
atatggggtg atgctttgtt tgatatcgtt gacaaagatc aaaatggagc cattacactg    480
gatgaatgga agcatacac caaagctgct ggtatcatcc aatcatcaga agatagcgag    540
gaaacattca gagtgagcga tattgatgaa agtggacaac tcgatgttga tgagatgaca    600
agacaacatt taggattttg gtacaccatg gatcctgcta gcgaaaagct ctacggtgga    660
gctgtcccct aagaagctct acggtggtga tgcaccctgg gaagatgatg tgattttgaa    720
taaaacactg atgaattcaa tcaaaatttt ccaaattttt gaacgatttc aatcgtttgt    780
gttgattttt gtaattagga acagattaaa tcgaatgatt agttgttttt ttaatcaaca    840
gaacttacaa atcgaaaaag t                                              861
```

<210> SEQ ID NO 4
<211> LENGTH: 189
<212> TYPE: PRT
<213> ORGANISM: Aequorea victoria

<400> SEQUENCE: 4

```
Val Lys Leu Thr Ser Asp Phe Asp Asn Pro Arg Trp Ile Gly Arg His
1               5                   10                  15

Lys His Met Phe Asn Phe Leu Asp Val Asn His Asn Gly Lys Ile Ser
            20                  25                  30

Leu Asp Glu Met Val Tyr Lys Ala Ser Asp Ile Val Ile Asn Asn Leu
        35                  40                  45

Gly Ala Thr Pro Glu Gln Ala Lys Arg His Lys Asp Ala Val Glu Ala
    50                  55                  60

Phe Phe Gly Gly Ala Gly Met Lys Tyr Gly Val Glu Thr Asp Trp Pro
65                  70                  75                  80

Ala Tyr Ile Glu Gly Trp Lys Lys Leu Ala Thr Asp Glu Leu Glu Lys
                85                  90                  95

Tyr Ala Lys Asn Glu Pro Thr Leu Ile Arg Ile Trp Gly Asp Ala Leu
            100                 105                 110

Phe Asp Ile Val Asp Lys Asp Gln Asn Gly Ala Ile Thr Leu Asp Glu
        115                 120                 125

Trp Lys Ala Tyr Thr Lys Ala Ala Gly Ile Ile Gln Ser Ser Glu Asp
    130                 135                 140

Ser Glu Glu Thr Phe Arg Val Ser Asp Ile Asp Glu Ser Gly Gln Leu
145                 150                 155                 160

Asp Val Asp Glu Met Thr Arg Gln His Leu Gly Phe Trp Tyr Thr Met
                165                 170                 175

Asp Pro Ala Ser Glu Lys Leu Tyr Gly Gly Ala Val Pro
            180                 185
```

<210> SEQ ID NO 5
<211> LENGTH: 662
<212> TYPE: DNA
<213> ORGANISM: Obelia longissima

<400> SEQUENCE: 5

```
acgatcgaac caaacaactc agctcacagc tactgaacaa ctcttgttgt gtacaatcaa     60
```

```
aatgtcttca aaatacgcag ttaaactcaa gactgacttt gataatccac gatggatcaa    120
aagacacaag cacatgtttg atttcctcga catcaatgga aatggaaaaa tcaccctcga    180
tgaaattgtg tccaaggcat ctgatgacat atgtgccaag ctcgaagcca caccagaaca    240
aacaaaacgc catcaagttt gtgttgaagc tttctttaga ggatgtggaa tggaatatgg    300
taaagaaatt gccttcccac aattcctcga tggatggaaa caattggcga cttcagaact    360
caagaaatgg gcaagaaacg aacctactct cattcgtgaa tggggagatg ctgtctttga    420
tattttcgac aaagatggaa gtggtacaat cactttggac gaatggaaag cttatggaaa    480
aatctctggt atctctccat cacaagaaga ttgtgaagcg acatttcgac attgcgattt    540
ggacaacagt ggtgaccttg atgttgacga gatgacaaga caacatcttg gattctggta    600
cactttggac ccagaagctg atggtctcta tggcaacgga gttccctaag cttttttcg     660 aa                                                                  662
```

```
<210> SEQ ID NO 6
<211> LENGTH: 195
<212> TYPE: PRT
<213> ORGANISM: Obelia longissima

<400> SEQUENCE: 6

Met Ser Ser Lys Tyr Ala Val Lys Leu Lys Thr Asp Phe Asp Asn Pro
1               5                   10                  15

Arg Trp Ile Lys Arg His Lys His Met Phe Asp Phe Leu Asp Ile Asn
                20                  25                  30

Gly Asn Gly Lys Ile Thr Leu Asp Glu Ile Val Ser Lys Ala Ser Asp
            35                  40                  45

Asp Ile Cys Ala Lys Leu Glu Ala Thr Pro Glu Gln Thr Lys Arg His
    50                  55                  60

Gln Val Cys Val Glu Ala Phe Phe Arg Gly Cys Gly Met Glu Tyr Gly
65                  70                  75                  80

Lys Glu Ile Ala Phe Pro Gln Phe Leu Asp Gly Trp Lys Gln Leu Ala
                85                  90                  95

Thr Ser Glu Leu Lys Lys Trp Ala Arg Asn Glu Pro Thr Leu Ile Arg
            100                 105                 110

Glu Trp Gly Asp Ala Val Phe Asp Ile Phe Asp Lys Asp Gly Ser Gly
        115                 120                 125

Thr Ile Thr Leu Asp Glu Trp Lys Ala Tyr Gly Lys Ile Ser Gly Ile
    130                 135                 140

Ser Pro Ser Gln Glu Asp Cys Glu Ala Thr Phe Arg His Cys Asp Leu
145                 150                 155                 160

Asp Asn Ser Gly Asp Leu Asp Val Asp Glu Met Thr Arg Gln His Leu
                165                 170                 175

Gly Phe Trp Tyr Thr Leu Asp Pro Glu Ala Asp Gly Leu Tyr Gly Asn
            180                 185                 190

Gly Val Pro
        195
```

AEQUORIN AND OBELIN MUTANTS WITH DIFFERING WAVELENGTHS AND BIOLUMINESCENCE

BACKGROUND OF THE INVENTION

1. Field of the Invention

This invention relates to the fields of bioluminescent labels for microanalysis and drug discovery.

2. Background

The increased demand for simultaneously detecting more than one analyte in physiological fluids has generated a greater interest in array detection methodologies. Accurate determination of several biomolecules in a sample allows a more accurate diagnosis. In these assays, the label that gives a distinguishable signal is one of the most important parts of the assay. For an array detection to be successful, each analyte must generate a distinguishable signal from the signals generated by the other analytes. Fluorescent labels have been previously used extensively in array detection. The inherent disadvantage of fluorescent detection for biological samples is the background fluorescence that is inherent with the nature of this type of labels.

Bioluminescent labels offer several advantages over fluorescence detection. Bioluminescent labels, being rare in nature, have much smaller interference from biological and other matrices. They are not also prone to photo degradation. The phenomenon of bioluminescence, unlike fluorescence, is relatively rare in biological systems, thus, the sample does not produce any significant background signal. However, the bioluminescent labels have similar emission characteristics i.e., they emit light at roughly the same wavelength. Therefore, wild-type bioluminescent labels are not useful for array detection. New proteins that are capable of producing light at different wavelengths would be very beneficial as labels in array detection.

Aequorin is a calcium sensitive photo protein isolated from the jellyfish, *Aequorea Victoria*. It is widely used as a label in immunoassays and to monitor intracellular levels of free calcium. The X-ray crystal structure of aequorin reveals three EF-hand $Ca^{2+}$-binding sites, a hydrophobic pocket in which the chromophore, coelenterazine, resides. In the presence of molecular oxygen, coelenterazine and apoaequorin form a stable aequorin complex. The addition of calcium causes a conformational change in the aequorin. This conformational change results in the oxidation of the non-covalently bound chromophoric unit, the coelenterazine to an excited coelenteramide. As the excited coelenteramide relaxes, light is emitted at 469 nm.

*Aequorea Victoria* uses the blue light emitted from aequorin as an excitation light source to stimulate the emission of green light from *Aequorea Victoria*'s more famous and scientifically ubiquitous protein, Green Fluorescent Protein (GFP). GFP has long been used as a label in various scientific fields. Extensive research concerning GFP's structural and photochemical properties has resulted in the production of many spectrally shifted GFP mutants. The spectral shifts in GFP have proved extremely useful, allowing for single well multiple analyte analysis, multicolor reporting of cellular processes, and FRET measurements to study protein-protein interactions Bacskai et al., J Biomed Opt. 2003 Jul; 8(3): 368-75.

An advantage of using aequorin and other bioluminescent proteins instead of GFP is that since the bioluminescence emitted by these proteins is measured over virtually zero background, the proteins can be detected at extremely low levels (levels less than $10^{-18}$ moles). Additionally, this photoprotein retains its bioluminescence in a variety of buffers with a number of different additives. It can be stored in solution at 4° C. for over a month while still retaining 85% of its original activity. Lyophilization of the protein allows for its storage up to one year. Accordingly, the creation of aequorin variants with significantly different emission maximum would result in a biochemical label that is superior to GFP.

Aequorin has been used extensively, most notably for detection of calcium concentrations in vivo and as a label in immunoassays and nucleic acid probe-based assays. It has been demonstrated that aequorin functions as highly sensitive labels in the determination of both large (Erikaku, *Biochem Biophys Res Commun* 1991, 174,1331-6; Zenno, *Biochem Biophys Res Commun* 1990, 171, 169-74; Jackson, *J Immunol Methods* 1996, 190, 189-97; Yeh, *Anal Biochem* 1996, 236, 126-33) and small biomolecules (Yan, *Anal Biochem* 1994, 223, 111-8; Feltus, *Anal Biochem* 1997, 254, 62-; Ramanathan, *Analytica Chemica Acta* 1998, 369, 181-188). Some examples of binding assays employing aequorin as a label include the determination of amplified cytokine products (Xiao, *J Immunol Methods* 1996, 199, 139-47), human chorionic gonadotropin, testosterone, thyrotropin (Sgoutos, *Clin. Chem.* 1995, 41, 1637-1643) and human tumor necrosis factor-α (Erikaku, *Biochem Biophys Res Commun* 1991, 174, 1331-6). A majority of these assays have been performed in a noncompetitive assay format in which the wild type photoprotein has been covalently coupled to antigenic molecules or antibodies. See also, e.g., Tsuji et al. (1986) "Site-specific mutagenesis of the calcium-binding photoprotein aequorin," Proc. Natl. Acad. Sci. USA 83:8107-8111; Prasher et al. (1985) "Cloning and Expression of the cDNA Coding for Aequorin, a Bioluminescent Calcium-Binding Protein," Biochemical and Biophysical Research Communications 126:1259-1268; Prasher et al. (1986) Methods in Enzymology 133:288-297; Prasher, et al. (1987) "Sequence Comparisons of cDNAs Encoding for Aequorin Isotypes," Biochemistry 26:1326-1332; Charbonneau et al. (1985) "Amino Acid Sequence of the Calcium-Dependent Photoprotein Aequorin," Biochemistry 24:6762-6771; Shimomura et al. (1981) "Resistivity to denaturation of the apoprotein of aequorin and reconstitution of the luminescent photoprotein from the partially denatured apoprotein," Biochem. J. 199:825-828; Inouye et al. (1989) J. Biochem. 105:473-477; Inouye et al. (1986) "Expression of Apoaequorin Complementary DNA in *Escherichia coli*," Biochemistry 25:8425-8429; Inouye et al. (1985) "Cloning and sequence analysis of cDNA for the luminescent protein aequorin," Proc. Natl. Acad. Sci. USA 82:3154-3158; Prendergast, et al. (1978) "Chemical and Physical Properties of Aequorin and the Green Fluorescent Protein Isolated from *Aequorea forskalea*" J. Am. Chem. Soc. 17:3448-3453; European Patent Application 0 540 064 A1; European Patent Application 0 226 979 A2, European Patent Application 0 245 093 A1 and European Patent Specification 0 245 093 B1; U.S. Pat. No. 5,093,240; U.S. Pat. No. 5,360,728; U.S. Pat. No. 5,139,937; U.S. Pat. No. 5,422,266; U.S. Pat. No. 5,023,181; U.S. Pat. No. 5,162,227; and SEQ ID Nos. 5-13, which set forth DNA encoding the apoprotein; and a form, described in U.S. Pat. No. 5,162,227, European Patent Application 0 540 064 A1 and Sealite Sciences Technical Report No. 3 (1994).

Of particular relevance to the subject matter are U.S. Pat. Nos. 5,798,441; 5,766,941; 5,744,579; 5,541,309; 5,491,084; 5,422,266; and 5,360,728. Deo et al., Anal Biochem. 2000 May 15; 281(1):87-94; Malikova et al., FEBS Lett. 2003 Nov 6; 554(1-2):184-8; Vysotski et al., Biochemistry.

2003 May 27; 42(20):6013-24; Bondar et al., Biochemistry (Mosc). 2001 Sep; 66(9):1014-8; Kurose et al., Proc. Natl. Acad. Sci. USA, January 1999; Ohmiya et al., FEBS, vol. 301, no. 2, pp. 197-201, April 1992; Ohmiya et al., FEBS, vol. 320, no. 3, pp. 267-270, April 1993; Lewis et al., Bioconjugate Chem. 2000, 11:65-70; U.S. Pat. No. 5,876, 995; all of which are incorporated by reference.

The use of aequorin as a label for multiple analyte single well analysis and multicolor reporting of cellular processes has been limited because of recombinant aequorin's single emission maximum wavelength of 469 nm. Wild type aequorin emits at a constant wavelength regardless which coelenterazine variant is used. By using different chromophore analogues, incorporation of non-natural amino acids and site-directed mutagenesis, the inventors have discovered a number of mutants that can be used to make superior biochemical labels because they have an bioluminescent emission shifted with respect to wild type aequorin.

Obelin is another bioluminescent protein from the marine hydroid *Obelia longissima* consisting of a single 22.2 kDA polypeptide chain. The primary sequences of obelin, aequorin and other photoproteins are highly homologous so presumably generate bioluminescence by a common chemical mechanism. There is also sequence homology in regions corresponding to the EF-hand structures of calcium-binding proteins such as calmodulin and troponin C, suggesting that some resemblance in three dimensional structures might also ensue. Obelin, along with a number of other photoproteins, is available in an efficient expression system.

All references cited within this document are explicitly incorporated by reference for all purposes.

SUMMARY OF THE INVENTION

One aspect of the invention relates to an isolated nucleic acid capable of hybridizing to SEQ ID NO: 3 under stringent conditions and encoding a protein which is capable of binding coelenterazine and molecular oxygen and emitting light, the protein having an isoleucine residue in a first position corresponding to position 132 of SEQ ID NO: 4.

Another aspect of the invention relates to an isolated nucleic acid capable of hybridizing to SEQ ID NO: 3 under stringent conditions and encoding a protein which is capable of binding coelenterazine and molecular oxygen and emitting light and having a non-natural amino acid incorporated into a position corresponding to 132 of SEQ ID NO: 4.

In one embodiment of this aspect of the invention the non natural amino acid is fluorotyrosine or fluorotryptophan. In a further embodiment the nucleic acid of claim 36 wherein the fluorotyrosine is 3-fluoro-1-tyrosine. In yet another embodiment, the non natural amino is 5-fluoro-1-tryptophan.

Another aspect of the invention relates to an isolated nucleic acid capable of hybridizing to SEQ ID NO: 3 under stringent conditions and encoding a protein which is capable of binding coelenterazine and molecular oxygen and emitting light, the protein having a cysteine residue in a first position corresponding to position 69 of SEQ ID NO: 4.

One embodiment of this aspect of the invention relates to an aequorin mutant protein conjugated to a flurophore. In another embodiment, the flourophore is IANBD ester.

Another aspect of the invention relates to an isolated nucleic acid capable of hybridizing to SEQ ID NO: 3 under stringent conditions and encoding a protein which is capable of binding coelenterazine and molecular oxygen and emitting light, the protein having a cysteine residue in a first position corresponding to position 70 of SEQ ID NO: 4.

One embodiment of this aspect of the invention relates to an aequorin mutant protein conjugated to a flurophore. In another embodiment, the flourophore is IANBD ester.

Another aspect of the invention relates to an isolated nucleic acid capable of hybridizing to SEQ ID NO: 3 under stringent conditions and encoding a protein which is capable of binding coelenterazine and molecular oxygen and emitting light, the protein having a cysteine residue in a first position corresponding to position 74 of SEQ ID NO: 4.

One embodiment of this aspect of the invention relates to an aequorin mutant protein conjugated to a flurophore. In another embodiment, the flourophore is IANBD ester.

Another aspect of the invention relates to an isolated nucleic acid capable of hybridizing to SEQ ID NO: 3 under stringent conditions and encoding a protein which is capable of binding coelenterazine and molecular oxygen and emitting light, the protein having a cysteine residue in a first position corresponding to position 76 of SEQ ID NO: 4.

One embodiment of this aspect of the invention relates to an aequorin mutant protein conjugated to a flurophore. In another embodiment, the flourophore is IANBD ester.

Another aspect of the invention relates to an isolated nucleic acid capable of hybridizing to SEQ ID NO: 3 under stringent conditions and encoding a protein which is capable of binding coelenterazine and molecular oxygen and emitting light, the protein having a phenylalanine residue in a first position corresponding to position 132 of SEQ ID NO: 4.

Another aspect of the invention relates to an isolated nucleic acid capable of hybridizing to SEQ ID NO: 3 under stringent conditions and encoding a protein which is capable of binding coelenterazine and molecular oxygen and emitting light, the protein having an tyrosine residue in a first position corresponding to position 86 of SEQ ID NO: 4.

Another aspect of the invention relates to an isolated nucleic acid capable of hybridizing to SEQ ID NO: 3 under stringent conditions and encoding a protein which is capable of binding coelenterazine and molecular oxygen and emitting light, the protein having a cysteine residue in a first position corresponding to position 66 of SEQ ID NO: 4.

Another aspect of the invention relates to an isolated nucleic acid capable of hybridizing to SEQ ID NO: 3 under stringent conditions and encoding a protein which is capable of binding coelenterazine and molecular oxygen and emitting light, the protein having a cysteine residue in a first position corresponding to position 65 of SEQ ID NO: 4.

Another aspect of the invention relates to an isolated nucleic acid capable of hybridizing to SEQ ID NO: 3 under stringent conditions and encoding a protein which is capable of binding coelenterazine and molecular oxygen and emitting light, the protein having a tyrosine residue in a first position corresponding to position 16 of SEQ ID NO: 4.

Another aspect of the invention relates to an isolated nucleic acid capable of hybridizing to SEQ ID NO: 3 under stringent conditions and encoding a protein which is capable of binding coelenterazine and molecular oxygen and emitting light, the protein having a tryptophan residue in a first position corresponding to position 82 of SEQ ID NO: 4.

Another aspect of the invention relates to an isolated nucleic acid capable of hybridizing to SEQ ID NO: 3 under stringent conditions and encoding a protein which is capable of binding coelenterazine and molecular oxygen and emitting light, the protein having a phenylalanine residue in a first position corresponding to position 82 of SEQ ID NO: 4.

Another aspect of the invention relates to kits comprising mutant aequorins disclosed herein and a coelenterazine selected from the group consisting of coelenterazine (CTZ) i, ip, h, hcp, cp, fcp, f, n, and native coelenterazine.

Another aspect of the invention relates to a method of identifying inhibitors of bond-breaking enzymes comprising immobilizing a fusion protein encoded by a fusion protein nucleic acid comprising any one of the nucleic acids of claims 1 to 13; operably linked to a second nucleic acid encoding a bond-breaking enzyme recognition site; in a first locus and a second locus; contacting said fusion protein with a candidate compound in the presence of the bond-breaking enzyme in said first locus; contacting said fusion protein with the bond-breaking enzyme in said second locus; and determining whether there is an increase in the intensity of light emission at said first locus relative to light emission in said second locus.

Another aspect of the invention relates to a method of identifying inhibitors of HIV-1 protease comprising: immobilizing a fusion protein encoded by a fusion protein nucleic acid comprising a nucleic acid capable of hybridizing to SEQ ID NO: 3 under stringent conditions and encoding a protein which is capable of binding coelenterazine and molecular oxygen and emitting light; operably linked to a second nucleic acid encoding an HIV-1 enzyme recognition site; in a first locus and a second locus; contacting said fusion protein with a candidate compound in the presence of the bond-breaking enzyme in said first locus; contacting said fusion protein with the bond-breaking enzyme in said second locus; and determining whether there is an increase in the intensity of light emission at said first locus relative to light emission in said second locus.

In one embodiment of this aspect of the invention, the recognition site is Ser-Glu-Asn-Tyr-Pro-Ile-Val (SEQ ID NO:5). In another embodiment, the fusion protein is conjugated to a fluorophore. In yet another embodiement, the fusion protein comprises a non-natural amino acid. In a further embodiment, the non-natural amino acid is fluorotyrosine and is at a position corresponding to 132 of SEQ ID NO: 4.

Another aspect of the invention relates to obelin mutants with altered emission patterns.

In one embodiment of this aspect of the invention, an isolated nucleic acid capable of hybridizing to SEQ ID NO: 5 under stringent conditions and encoding a protein which is capable of binding coelenterazine and molecular oxygen and emitting light, said protein having an serine residue in a first position corresponding to position 51, and a serine residue in a second position corresponding to position 75 of SEQ ID NO: 6.

Another embodiment of this aspect of the invention relates to an isolated nucleic acid capable of hybridizing to SEQ ID NO: 5 under stringent conditions and encoding a protein which is capable of binding coelenterazine and molecular oxygen and emitting light, said protein having an serine residue in a first position corresponding to position 67, and a serine residue in a second position corresponding to position 75 of SEQ ID NO: 6.

Another embodiment of this aspect of the invention relates to an isolated nucleic acid capable of hybridizing to SEQ ID NO: 5 under stringent conditions and encoding a protein which is capable of binding coelenterazine and molecular oxygen and emitting light, said protein having an serine residue in a first position corresponding to position 158 of SEQ ID NO: 6.

Another embodiment of this aspect of the invention relates to an isolated nucleic acid capable of hybridizing to SEQ ID NO: 5 under stringent conditions and encoding a protein which is capable of binding coelenterazine and molecular oxygen and emitting light, said protein having an serine residue in a first position corresponding to position 151 of SEQ ID NO: 6.

Another aspect of the invention relates to kit comprising the obelin mutants and a coelenterazine selected from the group consisting of CTZ i, ip, h, hcp, cp, fcp, f, n, and native coelenterazine.

Another aspect of the invention relates to a method of identifying inhibitors of bond-breaking enzymes comprising immobilizing a fusion protein encoded by a fusion protein nucleic acid comprising an obelin encoding nucleic acids operably linked to a second nucleic acid encoding a bond-breaking enzyme recognition site; in a first locus and a second locus; contacting said fusion protein with a candidate compound in the presence of the bond-breaking enzyme in said first locus; contacting said fusion protein with the bond-breaking enzyme in said second locus; and determining whether there is an increase in the intensity of light emission at said first locus relative to light emission in said second locus.

In one embodiment of this aspect of the invention, the inhibitors are inhibitors of HIV-1 protease.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. The present invention may be practiced without some or all of these specific details. In other instances, well known process operations have not been described in detail, in order not to unnecessarily obscure the present invention. Accordingly, the drawings and description are to be regarded as illustrative in nature, and not as restrictive.

BRIEF DESCRIPTION OF THE DRAWINGS

FIG. 1. is a table showing the emission wavelength maximum (nm) of aequorin mutants with coelenterazine analogues.

FIG. 2. is a graph showing the emission spectrum of native and Aeq3 (aequorin Mutant S) with CTZ i and hcp.

FIG. 6. is a graph showing the emission spectrum of native aequorin with coelenterazine analogues CTZ i, ip, h, hcp, cp, fcp, f and native CTZ.

FIG. 7. is a table showing the emission wavelength maximum (nm) of aequorin mutant Mutant S Y132I, Mutant S having a 3-fluoro-1-tyrosine aequorin or a 5-fluoro-1-tyrosine non-natural amino acid in position 132 in conjunction with coelenterazine analogues CTZ i, ip, n, h, hcp, cp, fcp, f and native CTZ.

FIG. 8. is a graph showing the emission spectrum of aequorin Mutant S with a 3-fluoro-1-tyrosine in position 132 with coelenterazine analogues CTZ i, f, n, fcp, h, cp, ip, hcp and native CTZ.

FIG. 9. is a graph showing the emission spectrum of aequorin Mutant S with a 5-fluoro-1-tyrosine in position 132 with coelenterazine analogues CTZ i, f, n, fcp, h, cp, ip, hcp and native CTZ.

FIG. 10. is a graph showing the emission spectrum of aequorin Mutant S Ala69Cys, aequorin Mutant S Gly70Cys, aequorin Mutant S Ala74Cys, and aequorin Mutant S Glu76Cys conjugated to the IANBD fluorophore.

FIG. 11. shows the cDNA sequence of wild type aequorin.

FIG. 12. shows the amino acid sequence of wild type aequorin.

FIG. 13. shows the cDNA sequence of aequorin Mutant S.

FIG. 14. shows the amino acid sequence of aequorin Mutant S.

FIG. 16. is an illustration of the structures of various coelenterazine analogues.

FIG. 17. shows a list of non-natural amino acids contemplated for use in the invention.

FIG. 18. shows the cDNA sequence of wild type obelin.

FIG. 19. shows the amino acid sequence of wild type obelin.

FIG. 20. Obelin mutants with Coelenerazine analogues

DETAILED DESCRIPTION OF THE INVENTION

Figure 3:
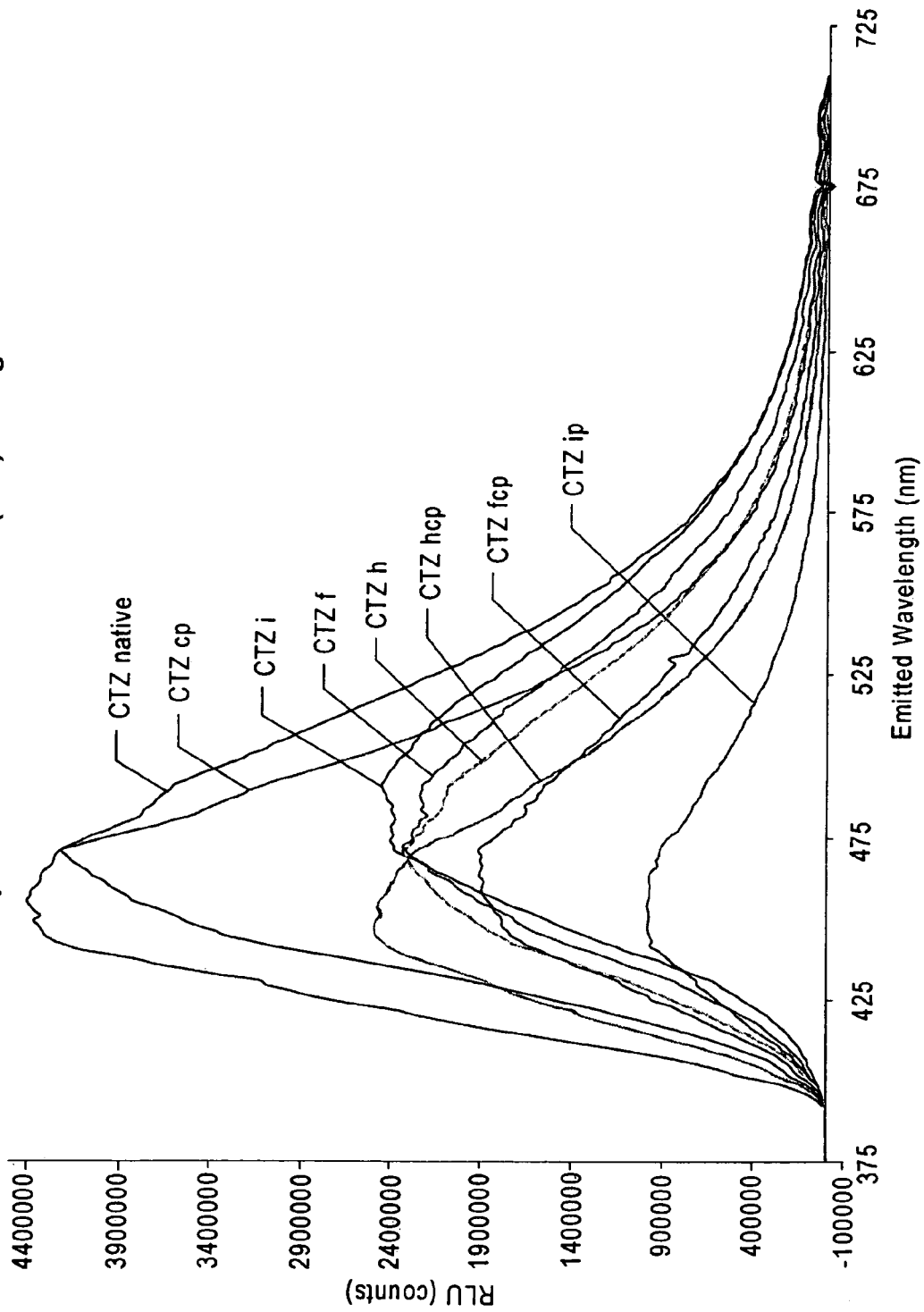
FIG. 3. is a graph showing the emission spectrum of Aeq3 with coelenterazine analogues CTZ i, ip, h, hcp, cp, fcp, f and native CTZ.
Figure 4:
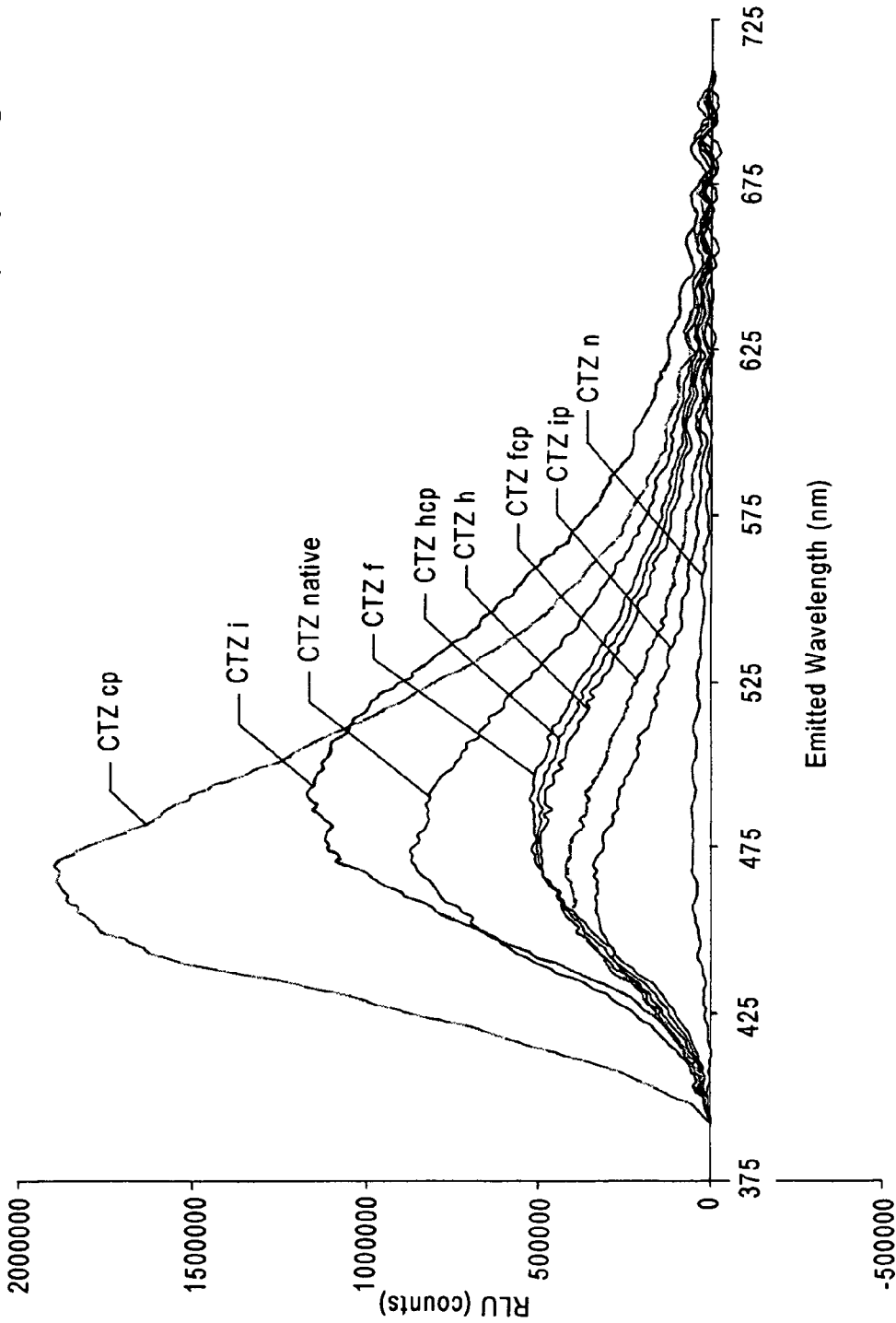
FIG. 4. is a graph showing the emission spectrum of Aeq5 (aequorin Mutant S with a Cys residue at position 5) with coelenterazine analogues CTZ n, cp, fcp, f, h, hcp, ip, i and native CTZ.
Figure 5:
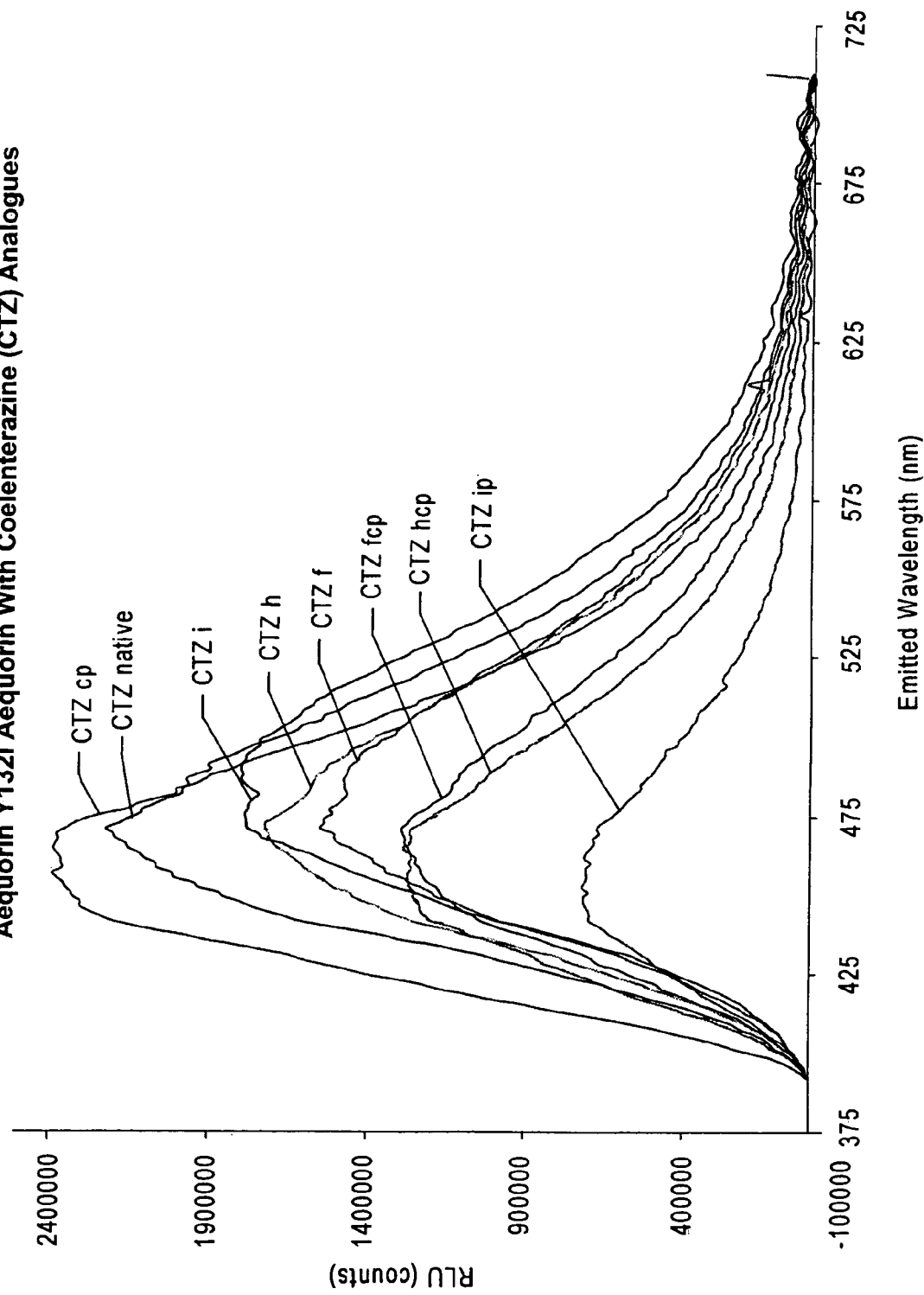
FIG. 5. is a graph showing the emission spectrum of aequorin Mutant S Y132I with coelenterazine analogues CTZ i, ip, h, hcp, cp, fcp, f and native CTZ.

There is a clear need for assays that can be adapted to the small volumes imposed by the new emerging microanalytical instrumentation. Bioluminescence provides a powerful detection system that can be employed in the development of assays with high sensitivity and very low detection limits. As the volumes become smaller, in order to be able to detect the target biomolecule, labels must become more sensitive and varied.

Accordingly, the subject invention provides aequorin and obelin mutants suitable for multianalyte microanalysis capable of emission of light at different wavelengths with respect to wild type.

Before describing the invention in greater detail the following definitions are set forth to illustrate and define the meaning and scope of the terms used to describe the invention herein:

"Emission" as used herein refers to photons emitted in a chemical reaction resulting from discrete energy states of electrons, as they pass from one excited level to another. Each photon emitted is associated with a fixed amount of energy expressed as a wavelength of light.

"Shifted emission" with respect to wild type as used herein refers to the fact that the aequorin mutants disclosed herein are capable of emitting light at a wavelength different, i.e., shifted from that of the wild type aequorin or obelin. The aequorin and obelin photoproteins consists of an apoprotein, a chromophoric unit (coelenterazine), and molecular oxygen, which when combined form a stable complex. Binding to $Ca^{2+}$ ions causes the photoprotein to undergo a conformational change, which results in the catalytic oxidation of the noncovalently bound coelenterazine. The coelenterazine is converted to coelenteramide with the release of $CO_2$ and a flash of light (λmax=about 469 to about 472 nm) lasting less than 10 s. The different structures of coelenterazine chromophores alone should result in spectral shifts since the energy difference between the excited coelenteramide and relaxed coelenteramide should change according to the structure of the original coelenterazine. Coelenterazine variants (e.g., i, ip, n, h, hcp, cp, fcp, f, native) have either different ring structure and/or functional groups attached. However, wild type aequorin emits at a constant wavelength regardless which coelenterazine variant is used (λmax=about 469 to about 472 nm). The mutants disclosed herein are capable of emitting light at a predictably shifted wavelength when used with various coelenterazine variants. For example, whereas FIG. 1 shows a wild type aequorin emissions peak of 472 nm regardless of which coelenterazine variant (i, ip, h, hcp, cp, fcp, f, n, or native) is used. Alternatively, aequorin Mutant S Y132I emits light at wavelengths ranging from 456 nm to 487 nm depending on the coelenterazine variant used.

"Chromophore" as used herein refers to group or substructure on a molecule that is responsible for the absorption of light. In the context of aequorin, the chromophore is coelenterazine (abbreviated CTZ) or an analog thereof. In addition to native coelenterazine there are several derivatives of coelenterazine designated i, ip, h, hcp, cp, fcp, f, or n. For chemical structures see FIG. 16.

The chromophore is stabilized by H-bonding to the three triads consisting of tyrosine, tryptophan, and histidine residues within the aequorin protein. Alteration of the strength of these H-bonds may affect the stability of the chromophore, inducing a change in the emission characteristics. The rationally designed aequorin and obelin mutants disclosed herein also shift the emission maximum wavelength by changing the electronic and H-bonding network within the chromophore binding pocket of aequorin. Combining aequorin and obelin mutants disclosed herein with various coelenterazine analogues allows for spectral shifting.

As used herein, "wild type" refers to the nucleic acid or amino acid sequence of a particular protein as it most commonly occurs in nature as a normal functional protein. Nonetheless, it is elementary to one of skill in the art that such functional proteins have allelic variations. An allele is one of several alternate forms of a gene that can have the same locus on homologous chromosomes and are responsible for alternative traits. Some alleles are dominant over others. Such normal variation is encompassed within this term. The wild type aequorin nucleic acid sequence is provided in SEQ ID NO: 1 and the wild type amino acid sequence is provided in SEQ ID NO: 2. The wild type obelin nucleic acid sequence is provided in SEQ ID NO: 5 and the wild type amino acid sequence is provided in SEQ ID NO: 6.

Aequorin "Mutant S" or "Aeq3" as used herein refers to an aequorin mutant where site-specific mutagenesis was used to replace the three cysteine residues with serine (at positions 145, 152, and 180). The starting point of the inventive aequorin mutants is aequorin Mutant S. Kurose et al., (Proc. Natl. Acad. Sci. USA, Vol. 86, pp. 80-84, Jan 1989), showed that the time required for the regeneration of the triply substituted aequorin was substantially increased compared to the time required for the regeneration of the wild-type aequorin. They also showed that cysteine plays an important role in the regeneration of aequorin but not in its catalytic activity. The aequorin Mutant S nucleic acid sequence is provided in SEQ ID NO: 3 and the aequorin Mutant S amino acid sequence is provided in SEQ ID NO: 4.

Of course, as will be obvious to one skilled in the art, various degenerate codons can be substituted into SEQ ID NO: 3 that will result in the identical amino acid sequence of SEQ ID NO: 4. All such substitutions of degenerate codons are equivalent because they result in identical amino acid sequences, and are, therefore, encompassed within the scope of the appended claims. Additionally, the sequence for apoaequorin is subject to significant microheterogeneity where variation in the amino acid and/or nucleotide sequence occurs at specific points in the sequence. Functional apoaequorin proteins may have variations relative to SEQ ID NO: 3 at one or more of the microheterogeneous residues. The positions of microheterogeneity, and the specific variations that occur at each, are shown in Table 1.

TABLE 1

POINTS OF MICROHETEROGENEITY IN THE APOAEQUORIN SEQUENCE.

| Residue | Amino Acid Variations |
| --- | --- |
| 4 | Glu, Lys |
| 12 | Ser, Pro |
| 15 | Asp, Asn |
| 18 | Arg, Lys |
| 37 | Lys, Arg |
| 70 | Glu, Gly |
| 71 | Ala, Asp |
| 85 | Asp, Glu |
| 88 | Glu, Ala |
| 95 | Arg, Lys |
| 98 | Ser, Thr |
| 99 | Glu, Asp, Cys |
| 102 | Lys, Glu |
| 103 | Lys, Arg |
| 105 | Ala, Ser |
| 108 | Glu, Gln |
| 109 | Pro, Ile |
| 114 | Ile, Leu |
| 123 | Val, Ile |
| 132 | Ser, Thr |
| 142 | Ala, Ser |
| 148 | Ser, Thr |
| 157 | Arg, Lys |
| 164 | Ser, Asn |

"Fluorophore" as used herein refers to a molecule capable of exhibiting fluorescence. The inventors have discovered that aequorin and obelin could be modified through the attachment of selected fluorophores capable of accepting energy transferred from aequorin. Preferably, fluorophores are chosen so the spectral bandwidth overlaps with the one corresponding to the bioluminescence emission of the Mutant S and wild type aequorin. Following energy transfer, the emission of light is shifted toward the maximum wavelength (λ) of emission of the attached fluorophore. Thus, by modifying the aequorins with different fluorophores, bioluminescent labels will be produced with different emission maxima, allowing for the simultaneous detection of multiple analytes.

The conjugation of the fluorophore can be directed towards the lysine residues on aequorin or oeblin by employing an N-hydroxysuccinimide ester derivative of the fluorophore. Alternatively, the fluorophore can be conjugated to unique cysteine residues introduced at sites on aequorin close to the coelenterazine binding site when a maleimide or an a iodoacetamide derivative of the fluorophore is employed.

Preferably, fluoroscein, nitrobenz-2-oxa-1,3-diazole (NBD) or (3-(4-carboxybenzoyl)quinoline-2carboxaldehyde (CBQCA), are employed as flurophores. More preferably, an iodoacetamide-derivative of the fluorophore, N-((2-iodoacetoxy)ethyl)-N-methyl)amino-7-nitrobenz-2-oxa-1,3-diaz-ole (IANBD ester) is attached to a unique cysteine rationally selected and inserted into aequorin Mutant S. Most preferably, an iodoacetamide-derivative of the fluorophore, N-((2-iodoacetoxy)ethyl)-N-methyl)amino-7-nitrobenz-2-oxa-1, 3-diazole (IANBD ester) is attached to a unique cysteine either at position 69, 70, 74 or 76 of aequorin Mutant S.

As used herein, "non-natural amino acid" refers to any amino acid that is chemically modified, preferably by the addition of a fluorine moiety, yet are similarly recognized by translation-competent enzymes and incorporated, site-specifically or otherwise, into proteins with marked effects on spectroscopic properties. Site-specific incorporation allows for the insertion of a non-natural amino acid at a specific place in the amino acid sequence. For example, this would allow for the placement of a non-natural tyrosine analog to be placed only at one position rather than replacing all tyrosine residues in a protein with the non-natural tyrosine analog. See Wang et al., Proc Natl. Acad. Sci. USA, 2003, 100, 56-61, Wang et al., J. Org. Chem., 2003, 68, 174-176, Zhang et al., Biochem. 2003, 42, 6735-6746. Fluorinated amino acids such as 3- and 5-fluorotyrosine and 5- and 6-fluorotryptophan are among the non-natural amino acids that can be incorporated into proteins by microorganisms at reasonable levels.

The incorporation of fluorinated aromatic amino acids such as of 3-fluoro-1-tyrosine, 5-fluoro-I-tyrptophan, and 6-fluoro-1-tyrptophan into aequorin alters the conformation of the protein, the H-bond network, and/or catalytic activity. Incorporation of 6-fluoro-1-tyrptophan resulted in an inactive aequorin, whereas, both 5-fluoro-1-tyrptophan and 3-fluoro-1-tyrosine displayed varied activity and shifted wavelengths. Fluorine atoms in tyrosine can also act as H-bond acceptors from —NH and —OH donors. This ability of fluorine facilitates fluorotyrosine residues in forming novel H-bonds, further stabilizing the structure. In aequorin, the stability of the chromophore residing within the hydrophobic pocket defines the spectral properties of aequorin and obelin, as well as their overall thermal stability. In aequorin, coelenterazine is stabilized by the H-bonds formed between the residues Tyr, His and Trp. The strength of these H-bonds defines the stability of coelenterazine. Therefore, incorporation of fluorinated residues such as tyrosine, tryptophan, and histidine should affect the spectral properties of aequorin.

Additional non-natural amino acids contemplated for use in the present invention are p-amino-L-phenylalanine, p-methoxy-L-phenylalanine, 2-nitro-L-tyrosine, 2-amino-5-hydroxy-4-methyl pentanoic acid. See FIG. 17.

Preferably, the non-natural amino acid to be incorporated into aequorin Mutant S is fluorotyrosine, more preferably 3-fluoro-L-tyrosine. Most preferably, fluorotyrosine is incorporated into position 132 of aequorin Mutant S.

In addition to fluorinated tyrosine, other moieties may change the acidity an amino acid for example of the phenolic proton in tyrosine. For example, nitro group at position 3, is a more effective electron acceptor, hence the pKa of phenolic proton would even be lower. A nitro group is also sterically more bulky therefore the spatial arrangement of the residues within the active site can change. An —OCH$_3$ group at position 2 in tyrosine, on the other hand, has an opposite effect due to the electron donating property of the group. Incorporation of non-natural amino acids into proteins can help expand the chemical and biological diversity of proteins In order to detect the inventive aequorin mutants, the use of an instrument capable of detecting flash-type bioluminescence over a wide range of wavelengths is envisaged. For example, a fiber optic sensor collects the bioluminescence signal emitted by the aequorin and transmits it to a grating that directs the beam of light to onto an optical array detector. In one embodiment, the system to acquire the spectra from the flash kinetics of aequorin and obelin luminescence consists of a microtiter plate reader. The optical path of the instrument is replaced with a high collecting efficiency fiber optic bundle. This fiberoptic bundle carries the emitted light into an Oriel Instruments Fixed Imaging Compact Spectrograph, the dispersed light is then fed into an ANDOR cooled CCD detector. See for example the SpectroSystem By Sciencewares, Inc (East Falmouth, Mass.).

The term "operably linked" refers to the linkage of a DNA segment to another DNA segment in such a way as to allow the segments to function in their intended manners. A DNA sequence encoding a gene product is operably linked to another DNA sequence encoding a different gene product when they are ligated in a manner which allows transcription and subsequent translation of both DNA sequences to yield a fusion protein. Preferably, such coding DNA sequences are linked "in frame." Additionally, a short stretch of coding DNA may be inserted between the two DNA sequences to encode a small number of spacer amino acids that facilitate proper functioning of the fusion protein by minimizing steric interference. Linkage of coding DNA sequences other coding DNA sequences or to regulatory sequences is typically accomplished by ligation at suitable restriction sites or via adapters or linkers inserted in the sequence using restriction endonucleases known to one of skill in the art.

Amino acid residue positions "corresponding" to one another as used herein, refers to the fact that there are conserved amino acid residues among orthologous proteins or among structurally similar aequorins that are encoded by substantially identical nucleic acids. Corresponding amino acids may be the same amino acids or they may be differing amino acids sharing one or more characteristics with respect to charge, polarity, acidity, hydrophilicity, hydrophobicity, or size. Corresponding amino acid positions may easily be determined in conjunction with standard protein alignment or 3-D modeling software common in the art. As such, one of skill in the art would readily be able to determine the location of other corresponding amino acids residues between properly aligned amino acid sequences encoded by nucleic acids that are substantially identical to one another.

The invention includes substantially identical polynucleotides that hybridize under stringent conditions (as defined herein) to all or a portion of the invention's mutant apoaequorin or obelin sequences (i.e., target sequences) or their complements. Under stringent hybridization conditions, only highly complementary, i.e., substantially similar nucleic acid sequences, hybridize. Preferably, such conditions prevent hybridization of nucleic acids having 4 or more mismatches out of 20 contiguous nucleotides, more preferably 2 or more mismatches out of 20 contiguous nucleotides, most preferably one or more mismatch out of 20 contiguous nucleotides. The hybridizing portion of the hybridizing nucleic acid is at least about 80%, preferably at least about 95%, or most preferably about at least about 98%, identical to the sequence of a target sequence, or its complement.

Hybridization of a nucleic acid to a nucleic acid sample under stringent conditions is defined below. Nucleic acid duplex or hybrid stability is expressed as a melting temperature ($T_m$), which is the temperature at which the probe dissociates from the target DNA. This melting temperature is used to define the required stringency conditions. If sequences are to be identified that are substantially identical to the probe, rather than identical, then it is useful to first establish the lowest temperature at which only homologous hybridization occurs with a particular concentration of salt (e.g. SSC or SSPE). Then assuming that 1% mismatching results in a 1° C. decrease in $T_m$, the temperature of the final wash in the hybridization reaction is reduced accordingly (for example, if sequences having >95% identity with the probe are sought, the final wash temperature is decrease by 5° C.). In practice, the change in $T_m$ can be between 0.5° C. and 1.5° C. per 1% mismatch.

Stringent conditions involve hybridizing at 68° C. in 5×SSC/5× Denhart's solution/1.0% SDS, and washing in 0.2×SSC/0.1% SDS at room temperature. Moderately stringent conditions include washing in 3×SSC at 42° C. The parameters of salt concentration and temperature be varied to achieve optimal level of identity between the primer and the target nucleic acid. Additional guidance regarding such conditions is readily available in the art, for example, Sambrook, Fischer and Maniatis, Molecular Cloning, a laboratory manual, (2nd ed.), Cold Spring Harbor Laboratory Press, New York, (1989) and F. M. Ausubel et al eds., Current Protocols in Molecular Biology, John Wiley and Sons (1994).

The invention relates to aequorin mutants that emit light at a wavelength shifted with respect to wild type aequorin. Table 1 below is a list of exemplary aequorin mutants inventors have discovered to have an emission profile shifted with respect to wild type.

| Mutant Name | Mutant Name |
| --- | --- |
| Mutant S Tyr132Ile | Mutant S Trp86Tyr |
| Mutant S Tyr132-fluorotyrosine | Mutant S Phe66Cys |
| Mutant S Ala69Cys | Mutant S Phe65Cys |
| Mutant S Gly70Cys | Mutant S His16Tyr |
| Mutant S Ala74Cys | Mutant S Tyr82Trp |
| Mutant S Glu76Cys | Mutant S Tyr82Phe |
| Mutant S Tyr132Phe | |

The invention also relates to obelin mutants that emit light at a wavelength shifted with respect to wild type obelin. Table 2 below is a list of exemplary obelin mutants inventors have discovered to have an emission profile shifted with respect to wild type.

| Mutant Name | Mutant Name |
| --- | --- |
| Cys75Ser/Cys51Ser | Cys158Ser |
| Cys75Ser/Cys67Ser | Cys151Ser |

One aspect of the invention relates to aequorin Mutants S that have been modified at position 132. As opposed to wild type aequorin which emits light at the same wavelength irrespective of the coelenterazine analogue used, these mutants' emission is varied with the use of different coelenterazine analogues. Embodiments of this aspect of the invention include but are not limited to Mutant S Tyr132Ile and Mutant S Tyr132Phe.

Another embodiment of this aspect of the invention is aequorin Mutant S with a non-natural amino acid in position 132. Preferably, the non-natural amino acid is a structural analogue of tyrosine. More preferably, the non-natural amino acid is fluorotyrosine or fluorotryptophan and most preferably, the fluorotyrosine is 3-fluoro-1-tyrosine.

Another aspect of the invention relates to aequorin Mutants S and obelin that have been modified at other amino acid positions. As opposed to wild type aequorin which emits light at the same wavelength irrespective of the coelenterazine analogue used, these mutants' emission is varied with the use of different coelenterazine analogues. Embodiments of this aspect of the invention include but are not limited to Mutant S Trp86Tyr, Mutant S Tyr82Trp, Mutant S His16Tyr, Mutant S Tyr82Phe, Mutant S Phe66Cys and Mutant S Phe65Cys and obelin mutants: Cys75Ser/Cys51Ser, Cys158Ser, Cys75Ser/Cys67Se, and Cys151Ser.

Another aspect of the invention relates to obelin and aequorin mutants that have been conjugated to a fluorophore which is excited by the emission of bioluminescent light from the aequorin such that it fluoresces at a different wavelength than wild type aequorin. Preferably, a fluorophore is selected that is excited by light having a wavelength similar to that at which wild type or Mutant S aequorin emits light. Aequorin Mutant S emits at a wavelength of about 445 nm to about 495 nm depending on the coelenterazine analogue employed. As such, it would be preferable to use a fluorophore that has an excitation wavelength between about 400 nm and about 520 nm, preferably, about 420 nm to about 500 nm and most preferably about 440 nm to about 495 nm. In one emobodiment of the invention, the native coelenterazine is used and therefore a flurophore having an excitation wavelength of about 469 nm to about 472 nm would be ideal. For example, an iodoacetamide-derivative of the fluorophore, N-((2-iodoacetoxy)ethyl)-N-methyl)amino-7-nitrobenz-2-oxa-1,3-diazole (IANBD ester) is employed. However, other fluorophores may be selected based on the coelenterazine that is to be used with aequorin mutant and the resulting shift in emission.

In another embodiment of this aspect of the invention, the fluorophore is conjugated to a unique cysteine inserted into the aequorin Mutant S primary structure. Preferably, the fluorophore is linked to the unique cysteine in aequorin Mutant S Ala69Cys, Mutant S Gly70Cys, Mutant S Ala74Cys, or Mutant S Glu76Cys. Most preferably, aequorin Mutant S Ala69Cys and Mutant S Gly70Cys are used.

In another aspect of the invention, the obelin or aequorin mutants are used in the development of different competitive and non-competitive assays for physiologically important molecules, such as peptides, drugs, etc., and for the high-throughput screening of biopharmaceuticals.

In one embodiment of this aspect of the invention, the obelin or aequorin mutant is tethered to an analyte by conventional covalent attachment. Preferably, attachment to an analyte of interest is mediated by the free amine groups of the lysine residues on the aequorin mutant. Preferably, pure apoprotein is be conjugated to an analyte of interest by reacting, for example, an N-hydroxysuccinimide derivative of the analyte with the lysine residues on the photoprotein (Kendall, *Trends Biotechnol* 1998, 16, 216-24). The commercial availability of a number of analytes that are already derivatized with N-hydroxysuccinimide derivatives makes this conjugation approach quite generic. Conjugation of these analytes through other derivatives is also possible and would be readily apparent to one of ordinary skill in the art.

Additionally, the attachment of other analytes to unique cysteines added to aequorin Mutant S may be accomplished in the following manner. Analytes of interest, such as digoxin, fluoxetine, phenytoin, phenobarbitone, theophyline, amitriptyline, chlomipramine and carbamezapine containing maleimido or iodoacetamide groups may be reacted with the modified apoaequorin using a sulfhydro-specific reaction. This reaction scheme may also be followed for analytes that are commercially available as maleimido or, iodoacetamide derivatives. If the ligands contain a free amino group, then they can be reacted with a heterobifunctional reagent, such as sulfosuccinimidyl 4-(N-maleimidomethyl)-cyclohexane-1-carboxylate (sulfo-SMCC) to introduce a maleimido coupling group (Hashida, *J. Appl. Biochem.* 1984, 56, 56-63). For example, a derivative of carbamazepine that contains a free amino group, carbamazepine-N-β-ethylamine will be prepared (Sidki, *Clin. Chem.* 1984, 30, 1348-1352). This derivative will then be coupled to sulfo-SMCC. If the ligand of interest contains a free carboxyl group, then a ligand hydrazide derivative will be prepared by reaction with thionyl chloride and hydrazine. This will introduce a free amino group, which can subsequently be reacted with sulfo-SMCC to introduce the desired maleimido moiety.

In another embodiment, the aequorin mutant proteins disclosed herein are part of a fusion protein wherein either the mutant obelin or aequorin cDNA and the cDNA of the target analyte are operably linked, i.e., transcribed and/or translated together in frame. Preferably, specifically designed oligonucleotide linkers may be employed to operably link the mutant aequorin cDNA to the cDNA of the target analye. Standard molecular biology techniques known to those of skill in the art enable the investigator to create expression vectors encoding such aequorin mutant—analyte fusion proteins.

Another aspect of the invention relates to methods of using the aequorin mutants disclosed herein to identify drug lead compounds. In one embodiment of the invention, candidate drug lead compounds are small molecules generated for example, by combinatorial chemistry techniques well documented in the art.

One embodiment of this aspect of the invention relates to a method of identifying compounds that inhibit bond breaking enzymes such as proteases. Proteases catalyze the cleavage of amide bonds of proteins producing small oligopeptides or free amino acids, and thus, these enzymes play a critical role in various cell processes. The actions of certain proteases within the cell are important in that they are involved in metabolic digestion, complement activation, fertilization, and the production of peptide hormones. For example, serine proteases are essential for coagulation and fibrinolysis in blood plasma. Therefore, considerable interest has been placed on the study of proteases and detecting the cleavage of peptide bonds.

In another embodiment of this aspect of the invention, the detection of protease activity involves the preparation of mutant aequorin fusion protein that will incorporate a recognition site for the particular bond breaking enzyme or protease within its structure that can be cleaved in the presence of the bond breaking enzyme or protease.

In another embodiment, this aspect of the invention relates to a method of identifying inhibitors of HIV-1 protease. The HIV-1 protease encoded by the human immunodeficiency virus plays a key role in the development of AIDS, and has been extensively studied. The protease has been identified as a prime target for the design of inhibitors to be used as potential treatment for the AIDS virus. The assay for the detection of HIV-1 protease activity involves the preparation of mutant aequorin fusion protein that will incorporate and thereby be operably linked to a recognition site for the protease within its structure that can be cleaved in the presence of the bond breaking enzyme. In one embodiment, the recognition site incorporated and tested for cleavage is Ser-Glu-Asn-Tyr-Pro-lle-Val (SEQ ID NO: 5), which corresponds to an optimum natural substrate for the HIV-1 protease located on the gag-pol polyprotein. Preferably, spacers amino acids will be introduced before and after the recognition site present within the fusion protein to limit the possibility of steric hindrance, and produce a more accessible cleavage site for the protease. Any of the mutant aequorins disclosed herein are suitable for use in this assay. Preferably, the fusion protein is prepared by ligating the operably linked mutant aequorin and recognition site DNAs into the expression vector pSD110 to yield pSD1001. Preferably, *Bacillus subtilis* cells is then transformed with the plasmid. The expressed protein is preferably purified using perfusion anion-exchange chromatography. The purity and concentration of the protein may be determined by SDS-PAGE and the bincinchoninic acid-based protein assay, respectively.

Figure 15:
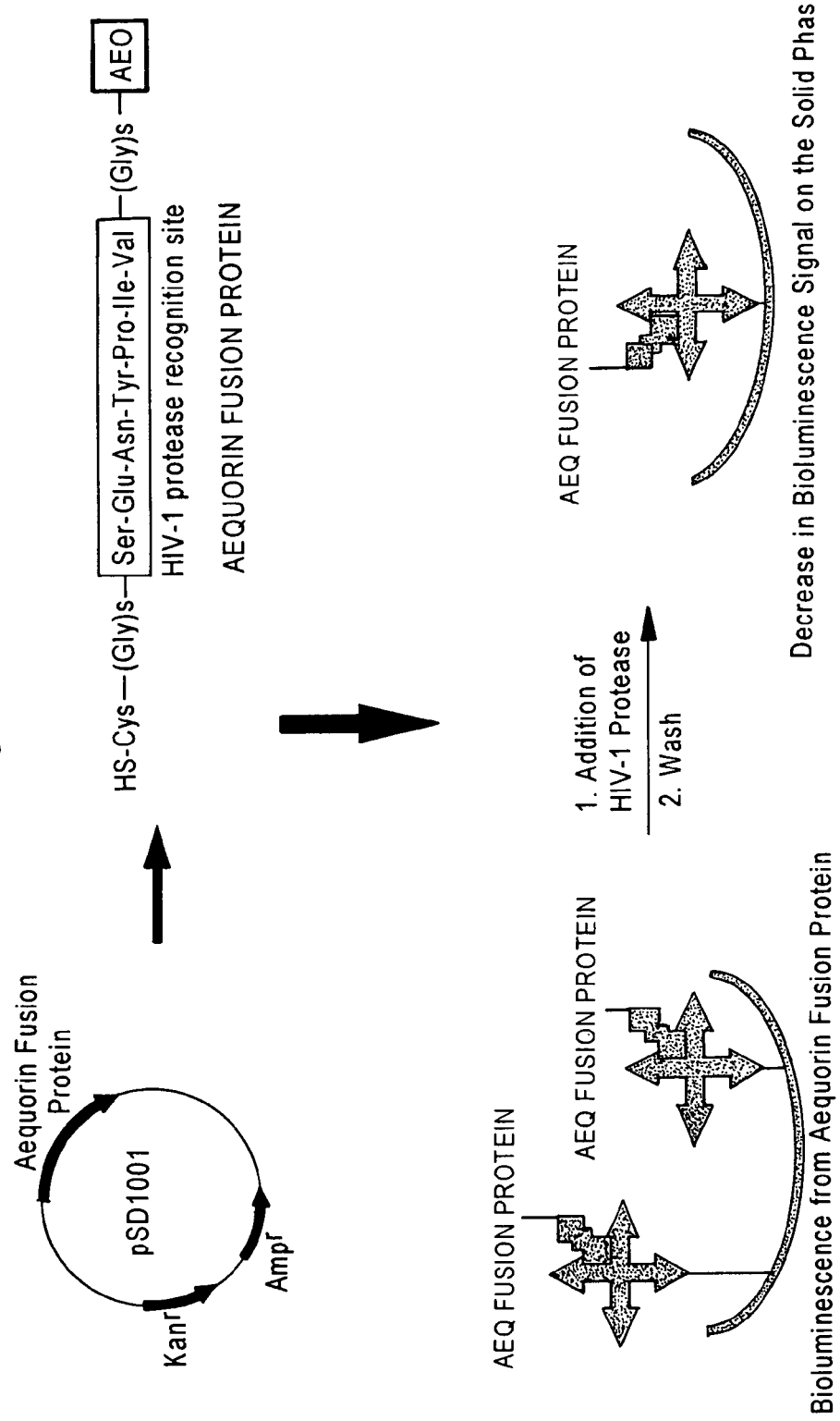
FIG. 15. is a cartoon illustrating the use of an aequorin fusion protein having an HIV-1 protease recognition site in an assay to identify inhibitors of HIV-1 protease.

Preferably, the purified fusion protein is biotinylated using a maleimide-activated biotin that reacts selectively with the unique sulfhydryl group at the N-terminus of the fusion protein. Following the biotinylation reaction, the aequorin fusion protein will preferably be generated by addition of an excess amount of coelenterazine. Preferably, the biotinylated fusion protein is immobilized onto a Neutravidin-coated 384-well microtiter plate. Bioluminescence studies are then undertaken to characterize the protein in terms of its luminescence properties. In order to determine the amount of the HIV-1 protease substrate to be used in subsequent experiments, preferably a binder-saturation study is performed. Preferably, the ability of the protease to cleave the recognition site is evaluated by using different concentrations of the enzyme on the substrate. To evaluate the bioluminescence system developed for assessing the activity of inhibitors of the HIV-1 protease, preferably a dose-response curve is generated for known inhibitors of this protease. Preferably, these include, for example, acetyl pepstatin and pepstatin A, competitive inhibitors of HIV-1 protease, as well as, a non-competitive inhibitor Ac-Leu-Val-phenylalaninal. At higher concentrations of the inhibitor, the bioluminescence signal should be higher since the protease be inhibited from cleaving at the recognition site. In contrast, as the concentration of the inhibitor decreases, the light intensity emitted by the solid phase should decrease because the protease will not be inhibited, and thus, it should catalyze the cleavage of the peptide bond (see FIG. 15).

Several strategies have been reported for the detection of amide bond cleavage by HIV-1 protease, including high performance liquid chromatography (HPLC), spectrophotometric analysis, fluorescence-based methods, ELISA with either chromogenic or fluorogenic substrate, and cell-based assays. Many of these methods employ synthetic substrates and require further confirmation of protease activity using naturally occurring substrates. These synthetic substrates may pose solubility problems in aqueous solutions at higher concentrations. In the proposed work, we postulate that a bioluminescence-based strategy can be employed in the sensitive detection of peptide bond cleavage by proteases. The assay designed should be readily adapted to automation, and is essentially a single step, direct assay for proteolytic bond cleavage. Another advantage of the methods taught herein is that the labeled-substrate for the protease is genetically engineered, which allows for the production of a highly reproducible labeled-substrate in unlimited quantities. Since the label used is a protein, the system does not suffer from any solubility problems under the aqueous conditions of the assay.

Furthermore, the methods taught herein detect protease activity are versatile in that different recognition sites for other physiologically and pharmacologically important proteases, such as caspases, could be incorporated into the assay design through the preparation of other bioluminescent fusion proteins. Moreover, the system may find application in the high-throughput screening of biopharmaceutical drugs that are potential inhibitors of a target protease.

EXAMPLE 1

Aequorin Mutants with Coelenterazine Analogues

Cysteine free aequorin (Mutant S), Y132I Mutant S aequorin, Aeq5 (Mutant S with a cysteine at position 5), and wild type Aequorin were purified and multiple spectra taken and averaged (See FIG. 1). Wild type aequorin showed the same emission maxima for all coelenterazines analogues. Mutant S had emission maximums ranging from 448 nm to 491 nm. Y132I Mutant S has emission maximums ranging from 453 nm to 487 nm. Aequorin 5 had emission maximums ranging from 466 nm to 491 nm. The greatest spread in emission maximum thus far has been between MutS/CTZ i and MutS/CTZ hcp (448 nm, 491 nm, respectively (43 nm range)). As can be seen on the graph the two peaks are starting to separate significantly. The greatest spread in emission maxima wavelengths so far with the same coelenterazine is CTZ hcp with Aeq5 (476 nm) and MutS (448 nm) being 28 nm. Also, the maximum spread with the same CTZ's and different aequorins is 19 nm for i, ip, and f.

Mutant S, Mutant S Y132I and Aeq 5 final emission spectrums were the result of the average of three trials. Wild type aequorins final spectrum was the result of two trials. All mutants, except Aeq5, were purified to >95% purity using SDS-PAGE and silver staining. All coelenterazine analogues were diluted to 100 micrograms/ML methanol. Solvent composition, coelenterazine concentration, temperature, and incubation time, were the same for all trials except with N coelenterazine, which required a higher concentration of aequorin than the other coelenterazines to show activity. Concentrations of the different mutants were not identical. Half life determination of Y132I Mut S with coelenterazines i, ip, h, hcp, cp, fcp, f, and native were 23, 0.9, 0.4, 0.2, 0.6, 0.7, 2.6, and 1.2 seconds, respectively.

The largest spread of emission wavelengths thus far is 43 nm between MutS/CTZi and MutS/CTZhcp. As can be seen on the graph this shift is starting to significantly separate the peaks. Further separation of the peaks will increase the practicality of the use of these mutant/ctz pairs. For single well multiple analyte analysis different aequorin mutants having separate emission maximums when using the same coelenterazine will be preferred. The 28 nm spread between Mut S and Aeq5 with CTZ hcp is the most promising for single well analysis applications thus far.

The emission spectrum of native recombinant aequorin encoded by SEQ ID NO: 1 and purchased commercially (Aqualite from Molecular Probes), showed identical emission maximum (472 nm) for all coelenterazine analogues, contrary to previously published results (Shimomura et al., Cell Calcium, (1993) 14:373-378). It is likely that the older, more indirect method of finding emission maximum used by Shimomura somehow yielded inaccurate results. Additionally, previously published results were obtained using protein that was isolated directly from jellyfish, leading to the collection of different protein isoforms yielding results different from the native recombinant form.

Interesting observations in the spectrum are the similarity in the shape and relative intensity of the emission spectrum of some mutants with the same coelenterazine. For example the CTZi spectrum with MutS and Y132I MutS are very similar in shape and relative intensity, yet in Aeq5 the CTZi spectrum shape and intensity is quite different. The most notable difference between these 3 mutants being that Aeq5 contains one cysteine whereas MutS and Y132I MutS contain none. Also, the maximum spread with the same CTZ's and different aequorins is 19 nm for CTZi, CTZip, and CTZf. CTZi and CTZfs similarity could be explained by the prescence of an electron withdrawing halogen in the same position, but the 19 nm spread in CTZip, with an aliphatic side chain in a different position, is curious.

EXAMPLE 2

Aequorin Mutants with Non-Natural Amino Acids

In order to incorporate selected non-natural amino acids into the aequorin, E. coli cells containing a plasmid that has the genetic information for aequorin were grown in minimal media. This medium was supplemented with essential amino acids and vitamins minus the amino acid of the analogue would be incorporated. After the cells were grown to a certain optical density the analogue and the inducer, IPTG, was added in order to express aequorin. As the protein expression takes place, the amino acid residues are replaced by the analogue present in the medium. The percent incorporation depends largely on the type and nature of the amino acid analogue used and can range from about 10 to about 75%. The, cells then were harvested by centrifuging and lysed by sonication. The cell debris was separated from the supernatant. This supernatant was then incubated with different coelenterazine analogues and the emission spectra were taken. The results are shown in the following table.

The results are shown in FIG. 7 which is a table showing the emission wavelength maximum (nm) of aequorin mutant Mutant S Y132I, Mutant S having a 3-fluoro-1-tyrosine aequorin or a 5-fluoro-1-tryptophan non-natural amino acid in position 132 in conjunction with coelenterazine analogues CTZ i, ip, n, h, hcp, cp, fcp, f and native CTZ. FIG. 8. is a graph showing the emission spectrum of aequorin Mutant S with a 3-fluoro-1-tyrosine in position 132 with coelenterazine analogues CTZ i, f, n, fcp, h, cp, ip, hcp and native CTZ. FIG. 9. is a graph showing the emission spectrum of aequorin Mutant S with a 5-fluoro-1-tyrosine in position 132 with coelenterazine analogues CTZ i, f, n, fcp, h, cp, ip, hcp and native CTZ. When 3-fluoro-I-tyrosine is incubated with coelenterazine i an emission wave length of 511 nm is observed. This to date is the largest shift observed in aequorin emission with respect to wild type aequorin.

EXAMPLE 3

Aequorin Mutants Conjugated to Fluorophores

The aequorin variants: Mutant S Ala69Cys, Mutant S Gly70Cys, Mutant S Ala74Cys, Mutant S Glu76Cys were generated by site-directed mutagenesis. The iodoacetamide-derivative of the fluorophore, N-((2-iodoacetoxy)ethyl)-N-methyl)amino-7-nitrobenz-2-oxa-1,3-diazole (IANBD ester) is attached to a unique cysteine either at position 69, 70, 74 or 76. This fluorophore was selected because it has a light absorption maximum of 472 nm which is close to the maximum emission of aequorin. IANBD ester has an emission wave length of 536 nm which is sufficiently far from wild type aequorin's emission of 469-472 nm to be easily detectable. Conjugation was performed using a malemide derivative of the fluorophore. The aequorin mutant—IANBD conjugation was incubated in excess of native coelenterazine and tested for photoemission by adding calcium ions. The results are in shown in FIG. 10. Labeled Mutant S Ala69Cys and Mutant S Gly70Cys showed and emission peak of the flurophore in the 530-540 nm range as well as a peak at corresponding to aequorin emission. When 3-fluoro-I-tyrosine is incubated with coelenterazine i an emission wave length of 511 is observed. This to date is the largest shift observed in aequorin emission with respect to wild type aequorin. This indicates that the transfer of energy from aequorin to the fluorophore occurred, thus resulting in a mutant aequorin with an emission shifted with respect to wild type aequorin.

EXAMPLE 4

Obelin Mutants with Coelenterazine Analogues

Obelin mutants C75S/C51/S, C75S/C67, C158S, C151S, and wild type obelin were purified and multiple spectra taken and averaged (See FIG. 20). Wild type obelin showed the same 469 nm emission maxima for all coelenterazines analogues. The results of the different obelin mutants used with different coelenterazines analogues is shown in FIG. 20.

What is claimed is:

1. An isolated nucleic acid having at least 95% sequence identity to SEQ ID NO: 3 wherein said nucleic acid encodes a protein that binds coelenterazine and molecular oxygen and emits light, said protein having a tryptophan residue in a first position corresponding to position 82 of SEQ ID NO: 4.

2. An isolated nucleic acid having at least 95% sequence identity to SEQ ID NO: 3 wherein said nucleic acid encodes a protein that binds coelenterazine and molecular oxygen and emits light, said protein having a phenylalanine residue in a first position corresponding to position 82 of SEQ ID NO: 4.

* * * * *